(12) United States Patent
Dai

(10) Patent No.: US 8,596,787 B2
(45) Date of Patent: Dec. 3, 2013

(54) SYSTEMS AND METHODS FOR PREDICTION OF OBJECTIVE VISUAL ACUITY BASED ON WAVEFRONT MEASUREMENTS

(75) Inventor: Guangming Dai, Fremont, CA (US)

(73) Assignee: AMO Manufacturing USA, LLC, Santa Ana, CA (US)

( * ) Notice: Subject to any disclaimer, the term of this patent is extended or adjusted under 35 U.S.C. 154(b) by 339 days.

(21) Appl. No.: 13/179,100

(22) Filed: Jul. 8, 2011

(65) Prior Publication Data

US 2011/0279774 A1 Nov. 17, 2011

Related U.S. Application Data

(60) Continuation-in-part of application No. 12/649,575, filed on Dec. 30, 2009, now Pat. No. 7,997,731, which is a division of application No. 12/013,763, filed on Jan. 14, 2008, now Pat. No. 7,699,470, which is a division of application No. 10/871,344, filed on Jun. 18, 2004, now Pat. No. 7,338,165.

(60) Provisional application No. 60/480,237, filed on Jun. 20, 2003.

(51) Int. Cl.
*A61B 3/10* (2006.01)
(52) U.S. Cl.
USPC .......................................... 351/212; 351/211
(58) Field of Classification Search
USPC .......................... 351/211, 212, 246, 205, 208
See application file for complete search history.

(56) References Cited

U.S. PATENT DOCUMENTS

| | | | |
|---|---|---|---|
| 4,257,689 A | 3/1981 | Yancy | |
| 4,646,207 A | 2/1987 | Levin et al. | |
| 5,054,908 A | 10/1991 | Katsumi et al. | |
| 5,579,063 A | 11/1996 | Magnante et al. | |
| 5,677,750 A | 10/1997 | Qi | |
| 5,777,719 A | 7/1998 | Williams et al. | |
| 5,779,341 A | 7/1998 | Chinniah et al. | |
| 5,864,381 A | 1/1999 | Neal et al. | |
| 5,936,720 A | 8/1999 | Neal et al. | |
| 6,052,180 A | 4/2000 | Neal et al. | |
| 6,086,204 A | 7/2000 | Magnante | |

(Continued)

FOREIGN PATENT DOCUMENTS

DE 4310561 A1 9/1994
JP 2002-087153 A 3/2002

(Continued)

OTHER PUBLICATIONS

Artal et al., "Retrieval of Wave Aberration of Human Eyes from Actual Point-Spread Function Data," Optical Society of America, Aug. 1998, 5:8, pp. 1201-1206.

(Continued)

*Primary Examiner* — Hung Dang
(74) *Attorney, Agent, or Firm* — AMO Manufacturing USA, LLC

(57) ABSTRACT

Methods, devices, and systems for predicting an optical acuity measure of an optical system of an eye. An optical acuity measure can be predicted by determining a point spread function based on a wavefront measurement of an eye, convolving a resolution target with the point spread function to produce an image, and predicting the optical acuity measure of the optical system of the eye based on the image.

20 Claims, 25 Drawing Sheets

(56) References Cited

U.S. PATENT DOCUMENTS

| | | | |
|---|---|---|---|
| 6,130,419 | A | 10/2000 | Neal et al. |
| 6,184,974 | B1 | 2/2001 | Neal et al. |
| 6,271,915 | B1 | 8/2001 | Frey et al. |
| 6,331,059 | B1 | 12/2001 | Kudryashov et al. |
| 6,338,559 | B1 | 1/2002 | Williams et al. |
| 6,450,663 | B1 | 9/2002 | Reinbach |
| 6,511,180 | B2 | 1/2003 | Guirao et al. |
| 6,547,391 | B2 | 4/2003 | Ross, III et al. |
| 6,547,395 | B1 | 4/2003 | Neal et al. |
| 6,550,917 | B1 | 4/2003 | Neal et al. |
| 6,572,230 | B2 | 6/2003 | Levine |
| 6,607,274 | B2 | 8/2003 | Stantz et al. |
| 6,619,825 | B2 | 9/2003 | Natsume |
| 6,672,746 | B2 | 1/2004 | Amano |
| 6,698,911 | B2 | 3/2004 | Naganawa et al. |
| 7,077,552 | B2 | 7/2006 | Ishida |
| 7,338,165 | B2 | 3/2008 | Dai |
| 7,357,509 | B2 * | 4/2008 | Williams et al. ............... 351/246 |
| 7,699,470 | B2 | 4/2010 | Dai |
| 7,997,731 | B2 | 8/2011 | Dai |
| 2002/0140902 | A1 | 10/2002 | Guirao et al. |
| 2002/0176051 | A1 | 11/2002 | Saladin |
| 2002/0186346 | A1 | 12/2002 | Stantz et al. |
| 2003/0038921 | A1 | 2/2003 | Neal et al. |
| 2003/0048413 | A1 | 3/2003 | Ross et al. |
| 2003/0156425 | A1 | 8/2003 | Turnbull et al. |
| 2009/0021694 | A1 | 1/2009 | Dai |
| 2010/0103376 | A1 | 4/2010 | Dai |

FOREIGN PATENT DOCUMENTS

| | | |
|---|---|---|
| JP | 2002-216506 A | 8/2002 |
| WO | WO 96/14793 A1 | 5/1996 |
| WO | WO 99/27334 A1 | 6/1999 |
| WO | WO 01/02822 A1 | 1/2001 |
| WO | WO 01/04590 A1 | 1/2001 |
| WO | WO 01/58339 A2 | 8/2001 |
| WO | WO 02/30273 A1 | 4/2002 |
| WO | WO 02/083078 A2 | 10/2002 |
| WO | WO 03/041609 A2 | 5/2003 |
| WO | WO 2004/096014 A2 | 11/2004 |

OTHER PUBLICATIONS

Artal, "Calculations of Two-Dimensional Foveal Retinal Images in Real Eyes," Optical Society of America, Aug. 1990, 7:8, pp. 1374-1381.

Barakat et al., "*The Computer in Optical Research*," (1980) 53-117.

Gaskill, "*Linear Systems, Fourier Transforms and Optics*," (1978) 334-339, 483-499.

Greivenkamp, J. E. et al., "Visual Acuity Modeling Using Optical Raytracing of Schematic Eyes", American Journal of Opthalmology, Opthalmic Publ., Chicago, IL, USA, vol. 120, No. 2, Aug. 1, 1995, pp. 227-240.

Liang et al., "Abberations and Retinal image Quality of the Normal Human Eye," Optical Society of America, Nov. 1997, 14:11, pp. 2873-2883.

Liang et al., "Objective Measurement of Wave Abberations of the Human Eye With the Use of a Hartmann-Shack wave-front sensor," Optical Society of America, A. Jul. 1994, 11:7, pp. 1949-1957.

Liang et al., "Supernormal Vision and High-Resolution Retinal Imaging Through Adaptive Optics," Optical Society of America, Nov. 1997, 14:11, pp. 2884-2892.

Miller, "Retinal Imaging and Vision at the Frontiers of Adaptive Optics," Physics Today, Jan. 2000, 7 pages total.

Williams et al., "Wavefront Sensing and Compensation for the Human Eye," (2000), pp. 287-310.

* cited by examiner

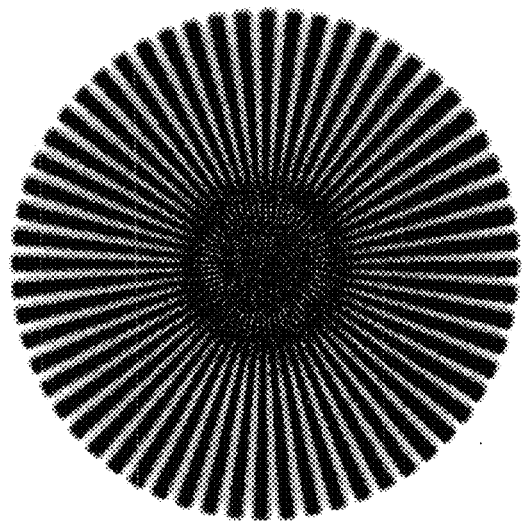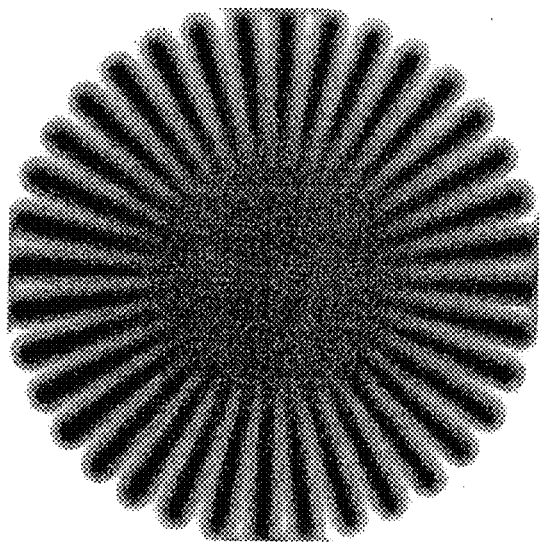
FIG. 9A  FIG. 9B
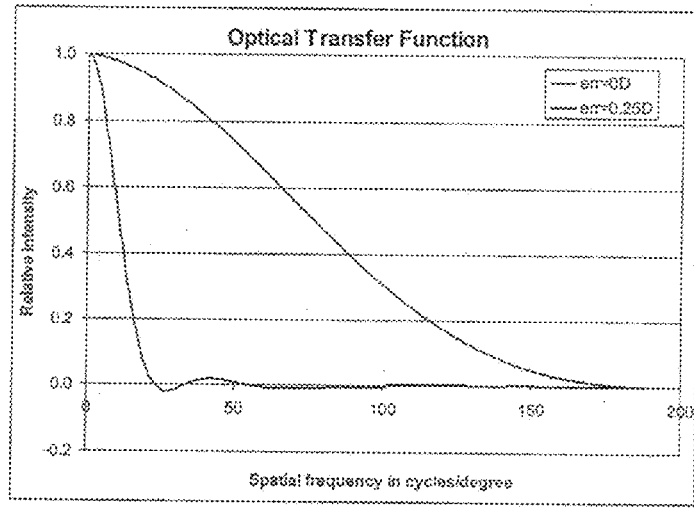
FIG. 9C

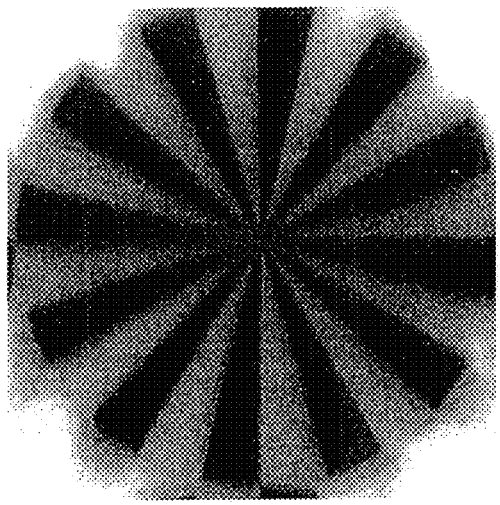 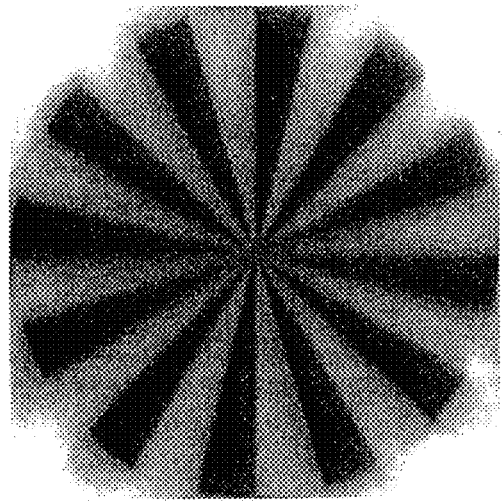
FIG. 11A　　　　　　　　　FIG. 11B
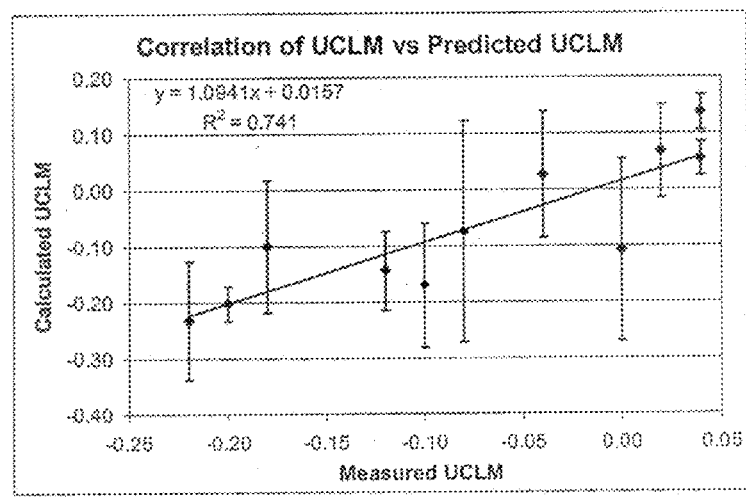
FIG. 12 tangential acuity or resolution radial acuity or resolution

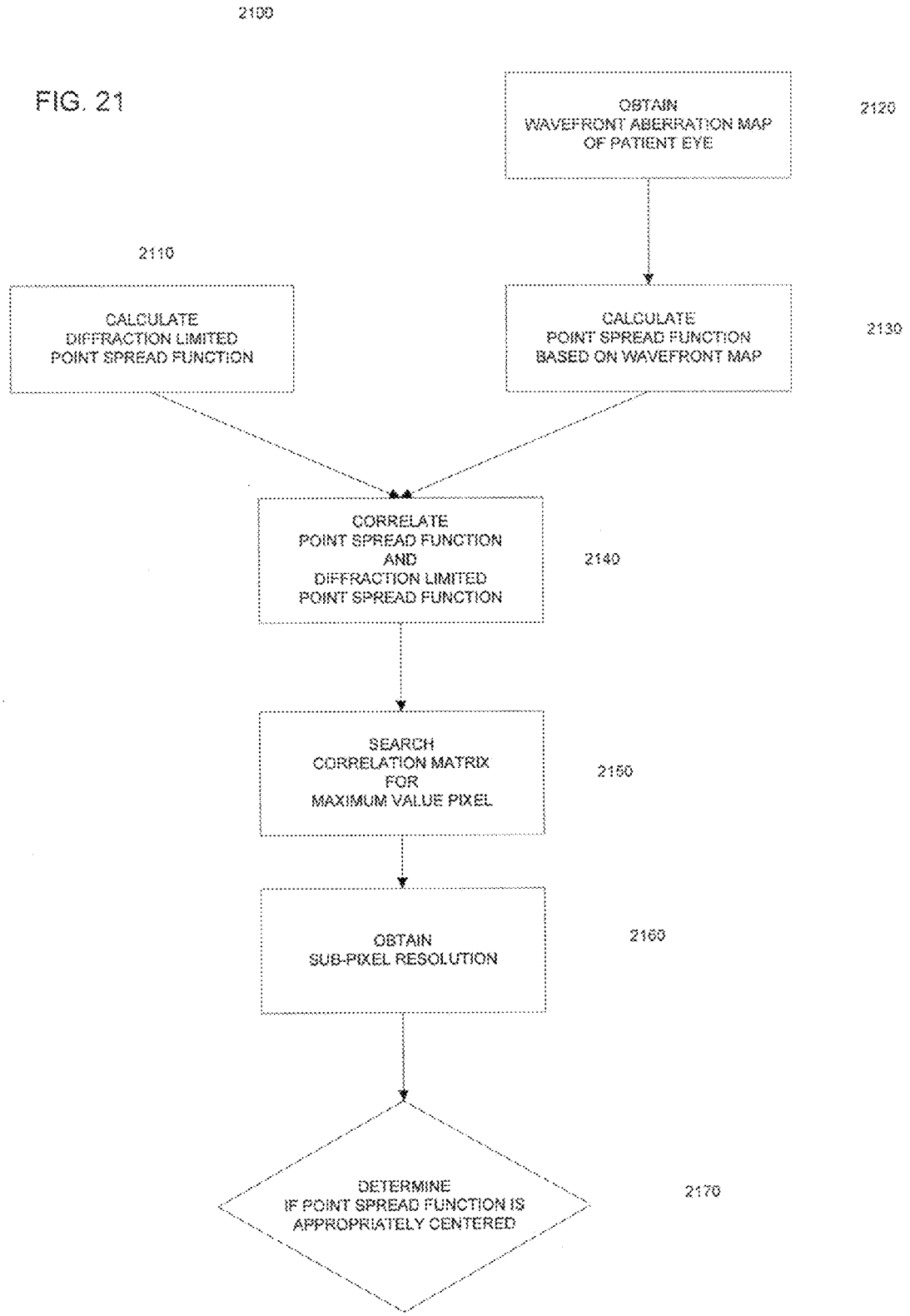

SYSTEMS AND METHODS FOR PREDICTION OF OBJECTIVE VISUAL ACUITY BASED ON WAVEFRONT MEASUREMENTS

CROSS-REFERENCES TO RELATED APPLICATIONS

This application is a continuation-in-part of U.S. patent Application Ser. No. 12/649,575, filed Dec. 30, 2009, now U.S. Pat. No. 7,997,731, which is a division of U.S. patent application Ser. No. 12/013,763, filed Jan. 14, 2008, now U.S. Pat. No. 7,699,470, which is a division of U.S. patent application Ser. No. 10/871,344, filed Jun. 18, 2004, now U.S. Pat. No. 7,338,165, which claims priority from U.S. Provisional Patent Application No. 60/480,237, filed Jun. 20, 2003. The entire disclosure of each of these applications is incorporated herein by reference for all purposes.

BACKGROUND OF THE INVENTION

This invention relates to optical system analysis, and in particular provides methods and systems for evaluating an optical acuity measure of an individual's eye.

The visual acuity of the eye can be affected by many factors. For example, visual acuity can be affected by objective factors such as the optical characteristics of the cornea and lens, as well as subjective factors such as light absorption and detection in the retina, and neural processing in the brain. Traditionally, measuring visual acuity of the human eye has involved methods using eye charts. The test results from such methods, however, can be subjective in nature as they involve the human brain's interpretation of vision, and therefore may not be representative of the quality of the eye's optics.

It would be desirable to have improved methods and systems that provide accurate and objective prediction and evaluation of an individual's visual acuity.

BRIEF SUMMARY OF THE INVENTION

The present invention provides methods, devices, and systems for predicting an optical acuity measure of an optical system of an eye. An optical acuity measure can be predicted by determining a point spread function based on a wavefront measurement of an eye, convolving a resolution target with the point spread function to produce an image, and predicting the optical acuity measure of the optical system of the eye based on the image.

In one aspect, embodiments of the present invention encompass systems and methods for determining an optical acuity measure of the eye. Exemplary techniques may include obtaining a wavefront map of the patient eye, calculating a point spread function based on the map, determining that the point spread function is centered, convolving a target with the centered point spread function to produce an image, and determining the optical acuity measure based on the image. In some cases, techniques may include, prior to determining that the point spread function is centered, determining that the point spread function is not centered and centering the point spread function. The process of centering the point spread function may include adjusting the point spread function toward a frame center of the wavefront measurement. In some cases, the process of centering the point spread function includes modifying a Zernike tip term and a Zernike tilt term of the wavefront measurement and adjusting the point spread function based on the modified Zernike terms. Optionally, the process of determining whether the point spread function is centered may include calculating a diffraction limited point spread function and correlating the point spread function with the diffraction limited point spread function to provide a correlation matrix. In some cases, techniques may further include searching the correlation matrix for a maximum pixel value. Techniques may also include obtaining a sub-pixel resolution of the correlation matrix.

In another aspect, embodiments encompass methods for determining an optical acuity measure of an eye which include obtaining a first point spread function based on a wavefront measurement of an eye, and determining whether the first point spread function is centered. If the first point spread function is centered, methods include convolving a target with the point spread function to produce an image, and determining the optical acuity measure of the eye based on the image. Or, if the first point spread function is not centered, methods include modifying a Zernike tip term and a Zernike tilt term of the wavefront measurement, obtaining a second point spread function based on the wavefront measurement with modified Zernike terms, determining that the second point spread function is centered, convolving a target with the second point spread function to produce an image, and determining the optical acuity measure of the eye based on the image. In some instances, the step of determining whether the first point spread function is centered comprises calculating a diffraction limited point spread function, and correlating the diffraction limited point spread function with the first point spread function to provide a correlation matrix. In some instances, methods further include searching the correlation matrix for a maximum value pixel. Optionally, methods include obtaining a sub pixel resolution measure based on the maximum value pixel. In some instances, the step of determining whether the first point spread function is centered includes determining whether a pre-determined metric is met. According to some embodiments, the pre-determined metric is a value within a range from about 0.1 microns to about 10 microns. Some methods may include generating a vision treatment for the eye based on the optical acuity measure. Some methods may include administering the vision treatment to the eye.

In some aspects, embodiments of the present invention encompass systems for determining an optical acuity measure of an eye. For example, a system may include a first module that obtains a first point spread function based on a wavefront measurement of an eye, a second module that determines whether the first point spread function is centered, a third module that convolves a target with the point spread function to produce an image and determines the optical acuity measure of the eye based on the image, if the first point spread function is centered, and a fourth module that modifies a Zernike tip term and a Zernike tilt term of the wavefront measurement, obtains a second point spread function based on the wavefront measurement with modified Zernike terms, determines that the second point spread function is centered, convolves a target with the second point spread function to produce an image, and determines the optical acuity measure of the eye based on the image, if the first point spread function is not centered. According to some embodiments, the second module determines whether the first point spread function is centered at least in part by calculating a diffraction limited point spread function, and correlating the diffraction limited point spread function with the first point spread function to provide a correlation matrix. According to some embodiments, the second module determines whether the first point spread function is centered at least in part by searching the correlation matrix for a maximum value pixel. According to some embodiments, the second module determines whether the first point spread function is centered at least in part by obtaining a sub pixel resolution measure based on the maximum value pixel. Optionally, the second module may determine whether the second point spread function is centered at least in part by determining whether a pre-determined metric is met. In some instances, the pre-determined metric is a value within a range from about 0.1 microns to about 10 microns.

In further aspects, embodiments of the present invention encompass computer program products for determining an optical acuity measure of an eye. For example, a computer program product may include a first code for accepting a first point spread function based on a wavefront measurement of an eye, a second code for determining whether the first point spread function is centered, a third code for convolving a target with the point spread function to produce an image and determining the optical acuity measure of the eye based on the image, if the first point spread function is centered, a fourth code for modifying a Zernike tip term and a Zernike tilt term of the wavefront measurement, obtaining a second point spread function based on the wavefront measurement with modified Zernike terms, determining that the second point spread function is centered, convolving a target with the second point spread function to produce an image, and determining the optical acuity measure of the eye based on the image, if the first point spread function is not centered, and a computer-readable medium that stores the codes. In some instances, the second code further includes code for calculating a diffraction limited point spread function, and for correlating the diffraction limited point spread function with the first point spread function to provide a correlation matrix. In some instances, the second code further includes code for searching the correlation matrix for a maximum value pixel. In some instances, the second code further includes code for obtaining a sub pixel resolution measure based on the maximum value pixel. In some instances, the second code further includes code for determining whether a pre-determined metric is met. Optionally, the pre-determined metric can be a value within a range from about 0.1 microns to about 10 microns.

In another aspect, the present invention provides a method for predicting an optical acuity measure of an optical system of an eye. The method can include determining a vision characteristic-modified point spread function based on a wavefront measurement of an eye; convolving a resolution target with the point spread function to produce an image; and predicting the optical acuity measure of the optical system of the eye based on the image. The resolution target can be selected from the group consisting of a single Snellen letter, a collection of Snellen letters, a plaid-type pattern, a resolution spoke, and an Archimedes spiral. The contrast of the resolution target can range from about 1% to about 100%. The contrast of the resolution target can range from about 10% to about 100%. The resolution target can be a resolution spoke having an angular spacing that ranges from about 5° to about 30°. The resolution target can be a resolution spoke having an angular spacing of about 15°. The resolution target can have a 512 pixel resolution. Relatedly, the resolution target can be a resolution spoke having an angular spacing greater than about 30°, and having a 1024 pixel resolution. The resolution target can also be a resolution spoke having an angular spacing of about 60, and having a 2048 pixel resolution. What is more, an optical resolution measure of the eye can be based on the image, and the optical acuity measure of the eye can be based on the optical resolution measure. The optical resolution measure of the eye can be based on Rayleigh's criterion as applied to the image. The optical resolution measure can be based on a sinusoidal interpretation of the addition of two Airy disks. Relatedly, discernability in the optical resolution measure can be based on a contrast ratio of the sinusoidal interpretation. The optical acuity measure can be represented in Snellen format. The optical resolution measure can be represented in log MAR format. The resolution target can be a resolution spoke, and the optical acuity measure can be calculated from a resolution ring calibration based on a 0.5 mm pupil diameter. The resolution target can be a resolution spoke, and the optical acuity measure can be calculated from a resolution ring calibration based on a defocused resolution spoke. The resolution target can be a resolution spoke, and the optical acuity measure can be based on a resolution ring calibration based on aberration-free cases of different pupil sizes ranging from about 0.25 mm to about 2 mm. The optical system of the eye can comprise a cornea and a lens of the eye. The point spread function can incorporate a parameter based on a planned ablative surgical procedure. The resolution target can be represented by a model. The image can be represented by a model.

In another aspect, the present invention provides a method for predicting an optical acuity measure of an optical system of an eye. The method can include determining a point spread function based on a wavefront measurement of an eye; centering the point spread function with respect to the center of the resolution target; convolving a resolution target with the point spread function to produce an image; and predicting the optical acuity measure of the optical system of the eye based on the image. The point spread function can be centered based on compensation for an averaged wavefront tilt. The point spread function can be centered based on the formulas $$\frac{\partial W(r,\theta)}{\partial x} = \frac{\partial}{\partial x}\sum_{i=1}^{N} c_i Z_i(r,\theta) = \sum_{i=1}^{N} c_i \frac{\partial Z_i(r,\theta)}{\partial x}$$

$$\frac{\partial W(r,\theta)}{\partial y} = \frac{\partial}{\partial y}\sum_{i=1}^{N} c_i Z_i(r,\theta) = \sum_{i=1}^{N} c_i \frac{\partial Z_i(r,\theta)}{\partial y}.$$

The point spread function can be centered based on implementation of a wavefront derivative as the average wavefront pixel difference between two neighboring pixels in either the x- or y-direction. The point spread function is centered based on the following formulas $$\frac{\partial W(r,\theta)}{\partial x} = \frac{1}{n}\sum_i \sum_j (W_{i,j+1} - W_{i,j}), (r \le 1)$$

$$\frac{\partial W(r,\theta)}{\partial y} = \frac{1}{n}\sum_i \sum_j (W_{i+1,j} - W_{i,j}), (r \le 1).$$

The point spread function can be centered based on a calculated center of gravity of the point spread function. The point spread function can be centered based on the following formulas $$a_x = \frac{\int\int x i(x,y)dxdy}{\int\int i(x,y)dxdy} = \frac{\sum_i \sum_j j I_{i,j}}{\sum_i \sum_j I_{i,j}}$$

-continued $$a_y = \frac{\iint yi(x,y)dxdy}{\iint i(x,y)dxdy} = \frac{\sum_i \sum_j i I_{i,j}}{\sum_i \sum_j I_{i,j}}.$$

The point spread function can be centered based on cross correlation between an input spoke and an output spoke. The point spread function can be centered based on the following formula $$c(a_x, a_y) = I(x,y) \oplus i(x-a_x, y-a_y).$$

In another embodiment, the present invention provides a method for determining an optical acuity measure of an optical system of an eye. The method can include determining a vision characteristic-modified point spread function based on a wavefront measurement of an eye; convolving a resolution target with the point spread function to produce an image; and determining the optical acuity measure of the optical system of the eye based on the image.

In yet another embodiment, the present invention provides a method for determining an optical acuity measure of an optical system of an eye. The method can include determining a point spread function based on a wavefront measurement of an eye; centering the point spread function with respect to the center of the resolution target; convolving a resolution target with the point spread function to produce an image; and determining the optical acuity measure of the optical system of the eye based on the image. The optical acuity measure can be determined by predicting the measure.

In still another embodiment, the present invention provides a method for planning an optical procedure for an eye based on a predicted optical acuity measure of the eye. The method can include determining a putative optical procedure for an eye; determining a vision-characteristic-modified point spread function based on a wavefront measurement of an eye and the putative optical procedure for the eye; and adjusting the putative optical procedure for the eye, such that a resolution target convolved with the point spread function produces an image that corresponds to an optimal optical acuity measure of the eye.

In another embodiment, the present invention provides a method for determining an estimated visual acuity of the eye. The method can include measuring visual distortion induced by optical aberrations of an eye of a patient to determine an imaging performance of the eye; constructing an acuity measurement model by simulating imaging performance of the eye for a resolution target; and determining an estimated visual acuity of the eye using the acuity measurement model. The estimated visual acuity of the eye can be determined such that the estimated acuity accurately correlates to an actual acuity of the eye.

In yet another embodiment, the present invention provides a system for predicting an optical acuity measure of an eye. The system can include a module that determines a vision-characteristic-modified point spread function based on a wavefront measurement of an eye; a module that convolves a resolution target with the point spread function to produce an image; and a module that predicts the optical acuity measure of the eye based on the image. The system can also include an input that accepts the wavefront measurement of the eye, and a module that determines the wavefront measurement of the eye.

In another embodiment, the present invention provides a system for determining an estimated optical acuity of an eye. The system can include a module that measures visual distortion induced by optical aberrations of an eye of an individual to determine an imaging performance of the eye; a module that constructs an acuity measurement model by simulating imaging performance of the eye for a resolution target; and a module that determines an estimated visual acuity of the eye using the acuity measurement model. The module that determines an estimated visual acuity can operate such that the estimated acuity accurately correlates to an actual visual acuity of the eye. The present invention also provides a kit that includes a system for predicting an optical acuity measure of an eye. The kit can also include instructions to use the system in predicting an optical acuity measure of an eye.

In yet another embodiment, the present invention provides a system for determining an optical acuity measure of an eye. The system can include a module that determines a vision-characteristic-modified point spread function based on a wavefront measurement of an eye; a module that convolves a resolution target with the point spread function to produce an image; and a module that determines the optical acuity measure of the eye based on the image.

In another embodiment, the present invention provides a system for determining an optical acuity measure of an eye. The system can include a module that determines a point spread function based on a wavefront measurement of an eye; a module that centers the point spread function with respect to the center of the resolution target; a module that convolves a resolution target with the point spread function to produce an image; and a module that determines the optical acuity measure of the eye based on the image.

In still another embodiment, the present invention provides a system for predicting an optical acuity measure of an eye. The system can includes a module that determines a point spread function based on a wavefront measurement of an eye; a module that centers the point spread function with respect to the center of the resolution target; a module that convolves a resolution target with the point spread function to produce an image; and a module that predicts the optical acuity measure of the eye based on the image.

In one aspect, embodiments of the present invention encompass systems and methods for determining an optical acuity measure of an eye. Exemplary methods may include, for example, obtaining a first point spread function based on a wavefront measurement of an eye, and determining whether the first point spread function is centered. Methods may further include convolving a target with the point spread function to produce an image, and determining the optical acuity measure of the eye based on the image, if the first point spread function is centered. Methods may also include modifying a Zernike tip term and a Zernike tilt term of the wavefront measurement, obtaining a second point spread function based on the wavefront measurement with modified Zernike terms, determining that the second point spread function is centered, convolving a target with the second point spread function to produce an image, and determining the optical acuity measure of the eye based on the image, if the first point spread function is not centered. In some cases, the step of determining whether the first point spread function is centered includes calculating a diffraction limited point spread function, and correlating the diffraction limited point spread function with the first point spread function to provide a correlation matrix. Some methods may include searching the correlation matrix for a maximum value pixel. Optionally, methods may include obtaining a sub pixel resolution measure based on the maximum value pixel. In some cases, the step of determining whether the first point spread function is centered includes determining whether a pre determined metric is met. Optionally, the pre determined metric may have a value within a range from about 0.1 microns to about 10 microns. In some embodiments, methods include generating a vision treatment for the eye based on the optical acuity measure. In some embodiments, methods may include administering the vision treatment to the eye.

In another aspect, embodiments of the present invention encompass systems for determining an optical acuity measure of an eye, where the systems include a first module that obtains a first point spread function based on a wavefront measurement of an eye, a second module that determines whether the first point spread function is centered, a third module that convolves a target with the point spread function to produce an image and determines the optical acuity measure of the eye based on the image, if the first point spread function is centered, and a fourth module that modifies a Zernike tip term and a Zernike tilt term of the wavefront measurement, obtains a second point spread function based on the wavefront measurement with modified Zernike terms, determines that the second point spread function is centered, convolves a target with the second point spread function to produce an image, and determines the optical acuity measure of the eye based on the image, if the first point spread function is not centered. In some cases, the second module determines whether the first point spread function is centered at least in part by calculating a diffraction limited point spread function, and correlating the diffraction limited point spread function with the first point spread function to provide a correlation matrix. In some cases, the second module determines whether the first point spread function is centered at least in part by searching the correlation matrix for a maximum value pixel. In some cases, the second module determines whether the first point spread function is centered at least in part by obtaining a sub pixel resolution measure based on the maximum value pixel. In some cases, the second module determines whether the first point spread function is centered at least in part by determining whether a pre determined metric is met. According to some embodiments, the pre-determined metric has a value within a range from about 0.1 microns to about 10 microns.

In yet another aspect, embodiments of the present invention encompass computer program products for determining an optical acuity measure of an eye. Exemplary computer program products may include a first code for accepting a first point spread function based on a wavefront measurement of an eye, a second code for determining whether the first point spread function is centered, a third code for convolving a target with the point spread function to produce an image and determining the optical acuity measure of the eye based on the image, if the first point spread function is centered, a fourth code for modifying a Zernike tip term and a Zernike tilt term of the wavefront measurement, obtaining a second point spread function based on the wavefront measurement with modified Zernike terms, determining that the second point spread function is centered, convolving a target with the second point spread function to produce an image, and determining the optical acuity measure of the eye based on the image, if the first point spread function is not centered, and a computer-readable medium that stores the codes. In some instances, the second code further includes code for calculating a diffraction limited point spread function, and for correlating the diffraction limited point spread function with the first point spread function to provide a correlation matrix. In some instances, the second code further includes code for searching the correlation matrix for a maximum value pixel. In some instances, the second code further includes code for obtaining a sub pixel resolution measure based on the maximum value pixel. In some instances, the second code further comprises code for determining whether a pre-determined metric is met. According to some embodiments, the pre-determined metric has a value within a range from about 0.1 microns to about 10 microns.

For a fuller understanding of the nature and advantages of the present invention, reference should be had to the ensuing detailed description taken in conjunction with the accompanying drawings.

BRIEF DESCRIPTION OF THE DRAWINGS

FIG. 9A shows a contrast reversal resolution spoke with 0.25D focusing error for a 6 mm pupil with angular spacing of 6°.

FIG. 9B shows a contrast reversal resolution spoke with 0.25D focusing error for a 6 mm pupil with angular spacing of 10°.

FIG. 9C shows an optical transfer function for the blurred resolution spoke shown in FIG. 6B.

FIG. 11A depicts a convolved resolution spoke without re-centration.

FIG. 11B depicts a convolved resolution spoke with re-centration.

FIG. 12 illustrates the correlation of the measured UCLM (uncorrected visual acuity with log MAR) versus the predicted UCLM for 11 LASIK eyes 1 year post surgery.

FIG. 21 shows aspects of a method for determining if a point spread function is appropriately centered according to embodiments of the present invention.

DETAILED DESCRIPTION OF THE INVENTION

Figure 1:
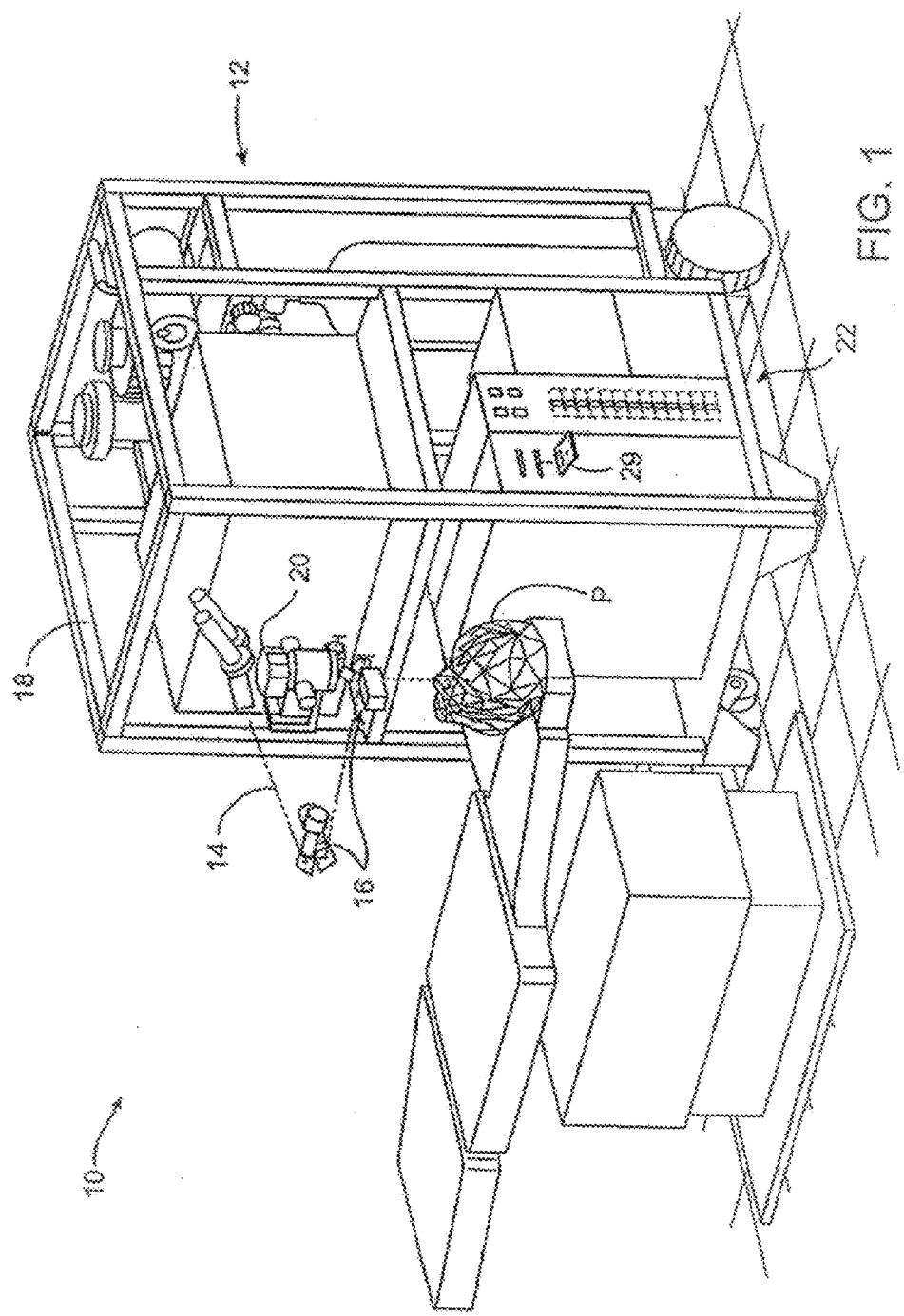
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
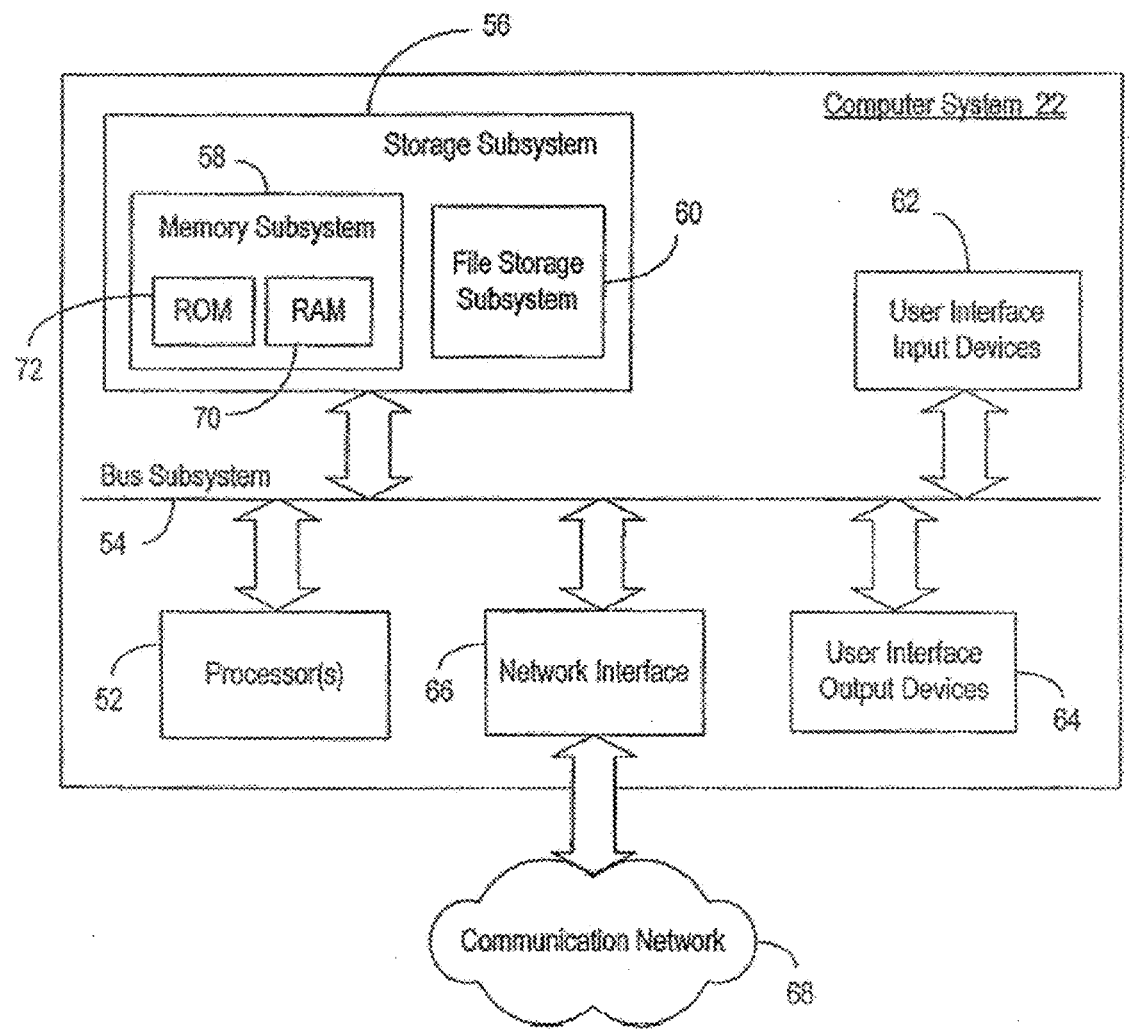
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
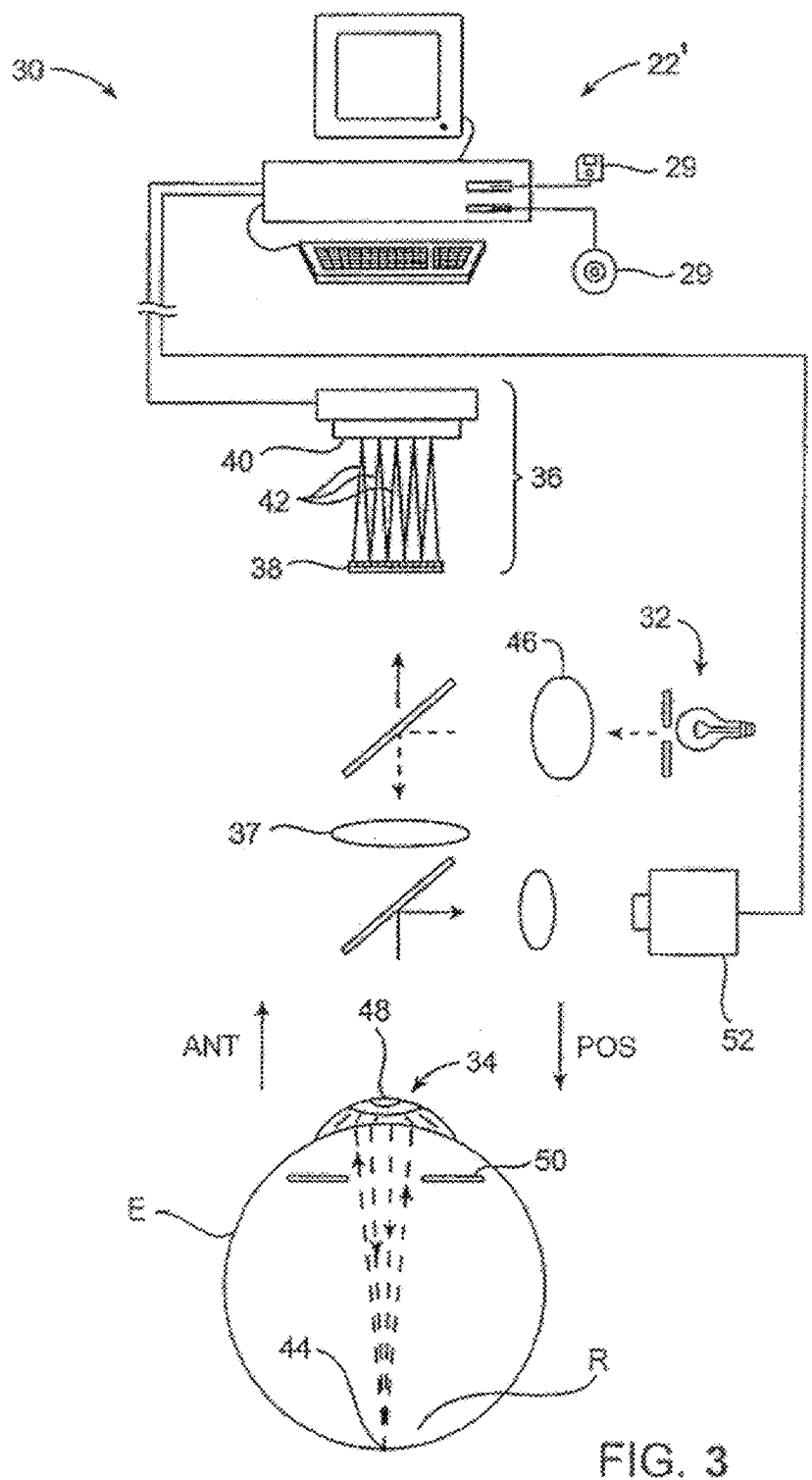
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot of image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
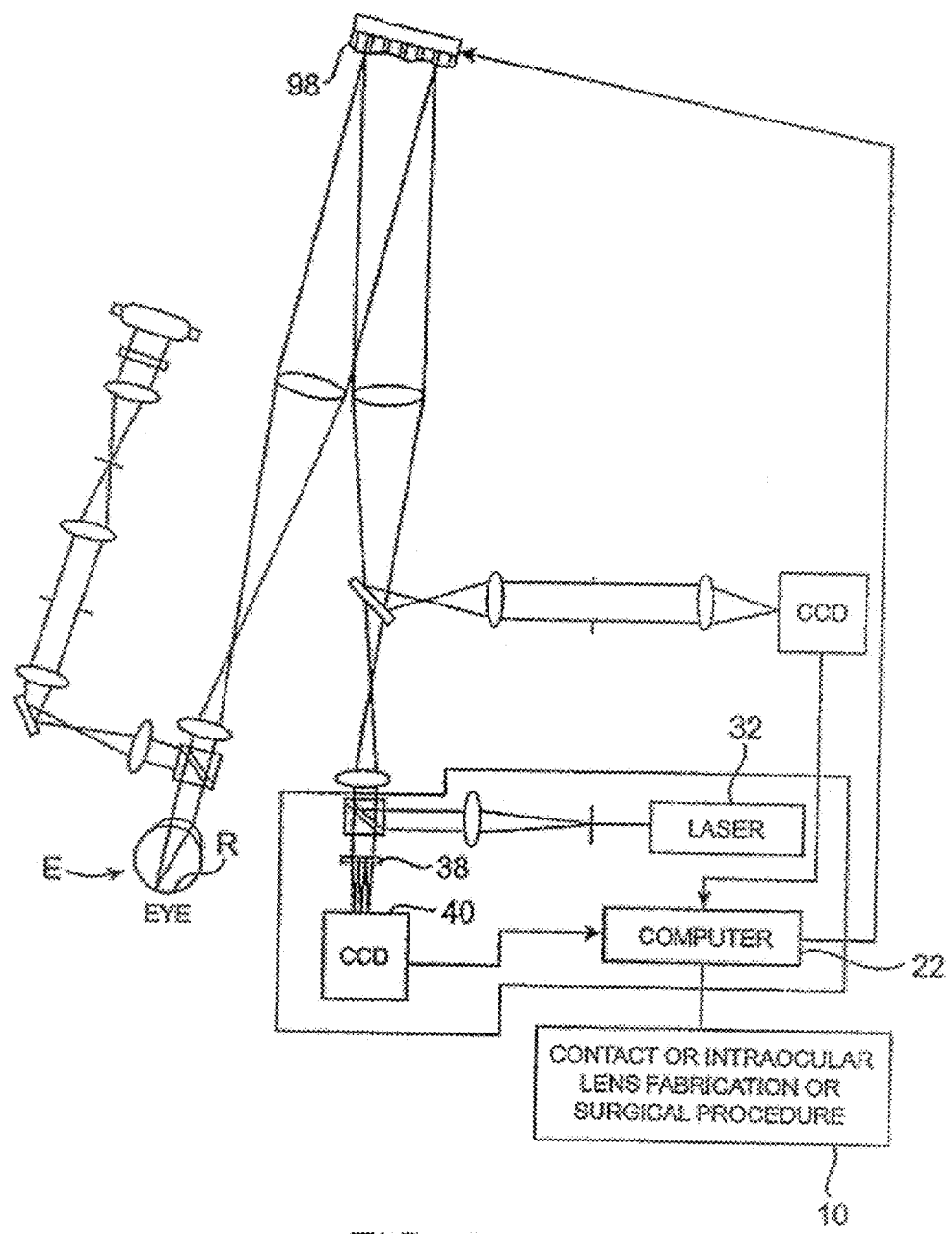
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a VISX WaveScan®, available from VISX, INCORPORATED of Santa Clara, Calif. One embodiment includes a WaveScan® with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention.

The present invention is useful for enhancing the accuracy and efficacy of photorefractive keratectomy (PRK), laser in situ keratomileusis (LASIK), laser assisted epithelium keratomileusis (LASEK), and the like. The present invention can provide enhanced optical correction approaches by improving the methodology for scaling an optical shape, or by generating or deriving new optical shapes, and the like.

The techniques of the present invention can be readily adapted for use with existing laser systems, including the VISX Excimer laser eye surgery systems commercially available from VISX of Santa Clara, Calif. Other suitable laser systems are manufactured by Alcon, Bausch & Lomb, Wavelight, Schwind, Zeiss-Meditec, Lasersight, Nidek and the like.

Standard point spread functions may sometimes be beneficial for determining visual acuity, but may not provide desirable results in some circumstances. It can be advantageous to specialize a point spread function to a particular optical system. For example, a particular optical system such as an eye may include factors such as chromatic aberrations, retinal sensitivity, or Stiles-Crawford effects that can affect vision characteristics, and it may be desirable to modify a point spread function based on these types of factors. Described herein are a number of approaches to modify a standard point spread function to arrive at a such a vision characteristic-modified point spread function.

The present invention allows predicting a measure of objective optical acuity that is based on the optical characteristics of the cornea and lens of a patient's eye. Specifically, the present invention provides systems, methods, and devices for determining the optical quality of an individual's eye, based on wavefront measurements. With the advent of wavefront technology, it has become possible to objectively and more accurately determine optical aberrations in the entire eye, including the cornea and the crystalline lens. Objective visual acuity, or optical acuity, can be predicted based on the wavefront measurements of human eyes.

The present invention can use a visual distortion measurement induced by optical aberrations of an individual's eye to determine an imaging performance of the eye. Often, the visual distortion measurement can be a vision characteristic-modified visual distortion measurement. An acuity measurement model can then be constructed by simulating the imaging performance of the eye for a resolution target. It is then possible to determine an estimated visual or optical acuity of the eye using the acuity measurement model. The visual acuity model can be estimated such that the estimated acuity accurately correlates to an actual visual or optical acuity of the eye. The imaging performance of the eye can be characterized in various ways, including point spread function and ray tracing approaches.

For example, the present invention will often involve determining a point spread function based on a wavefront measurement of an eye, convolving a resolution target with the point spread function to produce an image; and determining the measure of objective optical acuity of the eye based on the image.

Determining a Point Spread Function Based on a Wavefront Measurement of an Eye

In wavefront analysis, a highly collimated beam of light is projected on the retina, and the reflected outgoing beam is processed to create a wavefront aberration map. The aberration map represents aberrations introduced to the waveform as it passes through the optical system of the eye.

There are many known methods of processing the reflected outgoing beam to create the map. For example, in the Hartmann-Shack method, a single laser beam is projected as a spot on the retina. The reflected beam is captured by an array of small lenslets, which focus these rays into an array of spots on a cathode-coupling device (CCD) camera or other image capture device. The resulting spots are used to create the wavefront map. Wavefront measurement devices are commercially available, including the WaveScan® system available from VISX, Incorporated.

A useful feature of the wavefront aberration map is the point spread function (PSF), which can represent the visual distortion that a particular patient experiences with their current optical aberrations. In this way, the PSF can be used to predict or otherwise characterize the performance of an optical system. Generally, the PSF is based on the intensity distribution of an ideal point-like source in the focal plane resulting from the diffraction by the optics of the system. The PSF can be a three-dimensional graphic, or mathematical representation of the image of a point source produced by a lens or optical system.

With wavefront technologies, it is possible to calculate the point spread function (PSF) based on the optical path difference (OPD) of the optical system of the eye, where the optical system of the eye can include the cornea and lens. The optical path difference can be based on deviations in an incoming wave as compared to an ideal spherical ingoing wave. There are standard software packages available that take sensor data from wavefront devices and calculate the optical path difference and point spread function of the optical system.

Calculation of Point Spread Function

The point spread function (PSF) will typically be calculated based on the wavefront data. For example, a wavefront with aberrations can be denoted by $W(r, \theta)$. It is also possible to consider effects such as the polychromatic effect, the human eye's chromatic aberrations, the Stiles-Crawford effect, as well as the retinal spectral response function, when determining a point spread function, and in particular a vision characteristic-modified point spread function. Accordingly, many of the implementations of the point spread function described herein may not refer to a standard point spread function, but rather to a vision characteristic-modified point spread function. Considering these effects, for example, the polychromatic PSF can be expressed as $$PSF = \sum_{\lambda} R(\lambda) \left| FFT\left(P_{sc}(r) \exp\left[-j\frac{2\pi}{\lambda}[W(r, \theta) + \alpha D(\lambda)]\right]\right) \right|^2,$$

where $R(\lambda)$ is the retina spectral response function and can be approximated to $$R(\lambda) = e^{-300(\lambda - \lambda_0)^2}$$

and $P_{sc}(r)$ is the pupil apodization function (Stiles-Crawford effect) and can be written as $$P_{sc}(r) = 10^{-p\frac{r^2}{R^2}}$$

and $D(\lambda)$ is chromatic aberration at wavelength $\lambda$ and can be close to $$D(\lambda) = -21.587 + 92.87\lambda - 134.98\lambda^2 + 67.407\lambda^3$$

and the central wavelength $\lambda_0$ can be taken as 0.55 μm (as all wavelength units in the above formulae can be in μm). The pupil apodization strength parameter p can be taken as 0.06. α can represent the conversion factor from diopter to optical path difference (OPD). FFT can denote a fast Fourier transform and |*| denotes the module of a complex number.

In implementing the polychromatic wavelengths, it has been found that 7 wavelengths at 0.40, 0.45, 0.50, 0.55, 0.60, 0.65, and 0.70 μm, respectively, give adequate approximation for the entire white-light spectra.

Convolving a Resolution Target with the Point Spread Function to Produce an Image Once a point spread function or other visual distortion measurement has been determined based on a wavefront measurement of an eye, it is possible to simulate performance of the optical system, typically by convolving an object such as a resolution target with the PSF or other measurement to produce an acuity measurement model, often in the form of a blurred image. This is because the PSF is considered to be a good measure of the errors and artifacts that appear in an image produced by an optical system.

Construction of Resolution Targets

As noted above, resolution targets can be convolved with the point spread function as calculated from the wavefront measurements. It is useful to construct a resolution target in a way that determination of resolution or optical quality can be deduced from the blurred image of the target. A resolution target can include resolution lines or segments that are representative of a broad spectrum of spatial frequencies. It may also be desirable that a resolution target be capable of representing different contrast sensitivities. Often, resolution targets will be represented by mathematical or computer models, or otherwise constructed with software modules, hardware modules, or modules containing both software and hardware components.

A first resolution target technique is based on single eye chart letters, such as Snellen E, having different sizes. The size of the letter can be determined based on the size of the expected diffraction-limited point spread function (PSF). For instance, each horizontal stroke in a 20/20 letter E has an angular resolution corresponding to one arc minute. Thus, if the diffraction limited PSF is half an arc minute spanning four pixels, then each horizontal stroke in the letter E spans a width of eight pixels. Similarly, the height of each horizontal stroke, as well as the space between each horizontal stroke, is eight pixels. Thus, the height of the letter E spans 40 pixels (8*5). As the letter E is square, it also spans 40 pixels in width.

Figure 4A:
FIG. 4A shows a resolution target that includes the eye chart letter E corresponding to a visual acuity measure of 20/20.
Figure 4B:
FIG. 4B shows a resolution target of the eye chart letter E corresponding to a visual acuity measure of 20/40.
Figure 4C:
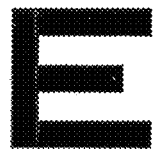
FIG. 4C shows a resolution target of the eye chart letter E corresponding to a visual acuity measure of 20/80.

FIGS. 4A, 4B, and 4C show resolution targets that include the eye chart letter E corresponding to a visual acuity measure of 20/20, 20/40, and 20/80, respectively. Resolution targets such as these can be used in the prediction or evaluation of objective optical acuity. Determination of an objective optical acuity with this approach typically involves multiple tests with resolution targets at varying sizes. Typically, larger letters that have been convolved with a point spread function are discernable. However, as the size of the letter decreases, the blurring effect of convolution can become more significant. In determining optical acuity, this approach can involve determining the resolution target size at which the blurred image is barely discernable.

Figure 4D:
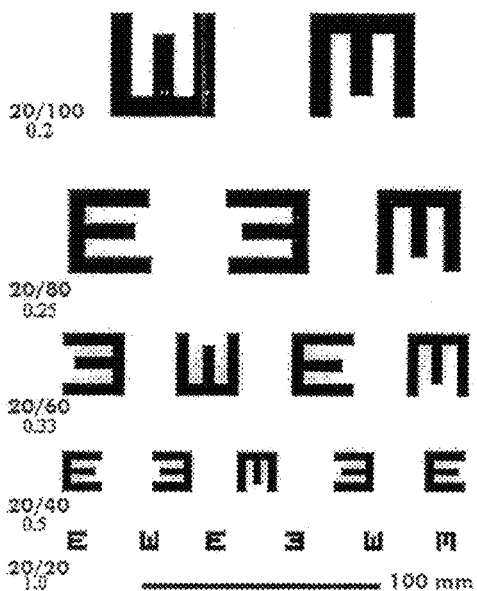
FIG. 4D shows a resolution target of an eye chart that includes the eye chart letter E corresponding to visual acuity measures of 20/20, 20/40, 20/60, and 20/80.

A second resolution target technique involves the use of an entire eye chart as the resolution target, as shown in FIG. 4D, which includes the eye chart letter E corresponding to visual acuity measures of 20/20, 20/40, 20/60, and 20/80. The entire eye chart can be convolved with the point spread function (PSF), and resolution can be estimated by evaluating the contrast loss in different size letters.

Figure 5A:
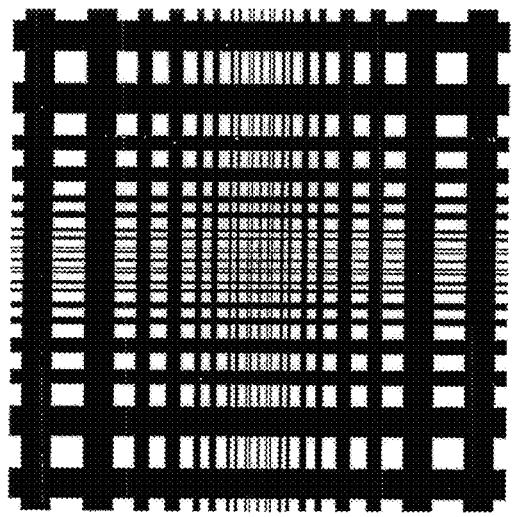
FIG. 5A illustrates a plaid-type resolution target at high resolution contrast.

A third resolution target technique involves the use of a plaid-type pattern resolution chart. Such a resolution target can be at high contrast, as shown in FIG. 5A (100% contrast), and at low contrast, as shown in FIG. 5 (10% contrast).

Figure 5B:
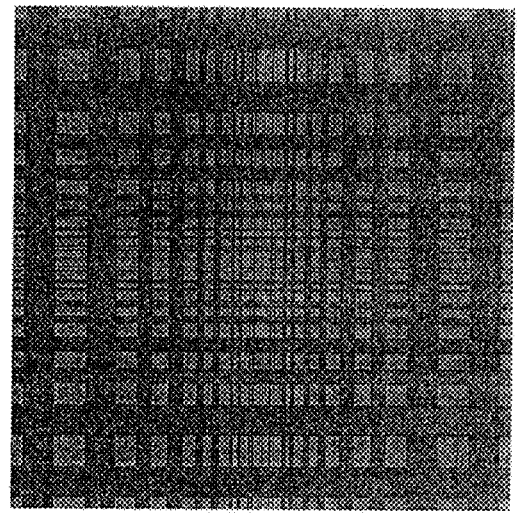
FIG. 5B illustrates a plaid-type resolution target at low resolution contrast.

The finest lines with the highest spatial resolution or frequency (for example, one pixel width), are usually disposed in the middle of the chart. Traveling outward from the middle, the resolution lines can be incrementally larger in size and spacing. For example, the next resolution lines can correspond to one half the spatial resolution or frequency of the immediate inner lines. If this progression is followed, as shown in FIGS. 5A and 5B, the outermost resolution lines can be 32 times larger, or 32 pixels in width. Thus, for example, if the finest lines can represent 20/10 visual acuity, the thickest lines can represent 20/320 visual acuity.

Convolution of plaid-type charts with the point spread function provides a blurred image that can be used to determine the optical acuity of the eye. As compared to the eye letter chart, plaid charts may be devoid of orientation bias. For example, the letter E is more biased in horizontal orientation, as it has three horizontal strokes and one vertical stroke. The plaid type resolution target approach typically involves evaluating several resolution lines in order to estimate the optical acuity. Also, as the lines are typically incremented in size, for example doubling in size going from the inside to the outside, the acuity measurement results are correspondingly incremented. For example, with such charts, it may be possible to obtain acuity of 20/10, 20/20, 20/40, 20/80, 20/160 and so on.

Figure 6A:
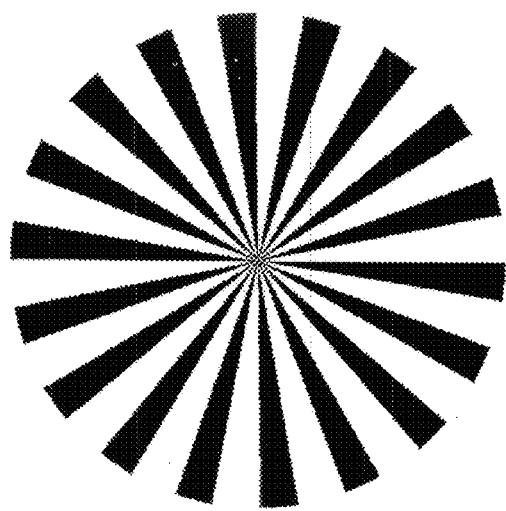
FIG. 6A depicts a resolution spoke type of resolution target at high resolution contrast.

A fourth resolution target technique involves the use of a resolution spoke constructed with continuous resolution from center (highest resolution) to periphery (lowest resolution). FIG. 6A illustrates a resolution spoke with 20° spacing and 100% contrast. The letter charts discussed above contain uniform lines and typically correspond only to discrete spatial frequencies, whereas a resolution spoke resolution target can have lines corresponding to a range of spatial frequencies. In other words, the change in spatial resolution of the spoke lines is substantially continuous, with higher resolution toward the center of the spoke, and lower resolution toward the outer periphery of the spoke. In some cases, the resolution may not be precisely continuous, however, as the resolution spoke target, the convolved image thereof, or both, may be pixelized. Once the resolution target is convolved with the point spread function, it is possible to determine circles that correspond to optical acuity measurements. Thus, the optical acuity can be determined with very fine stepping.

Figure 6B:
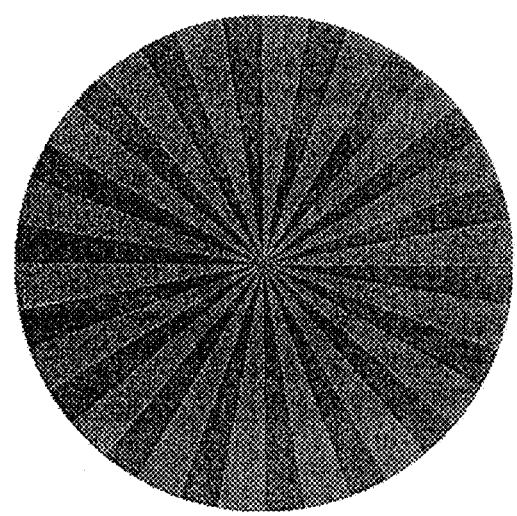
FIG. 6B depicts a resolution spoke type of resolution target at low resolution contrast.

The angular spacing can be controlled according to the desired resolution. For instance, when the spoke is to be used for very accurate, low aberration acuity testing, the angular spacing can be very small to construct very fine spokes. On the other hand, if the target is to use the resolution spoke to predict a large resolution range, then the angular spacing can be much larger. The resolution spokes illustrated here are constructed with different angular spacing and contrast. In many of the examples provided herein, a 30° is used in the calculations. In terms of resolution contrast, FIG. 6A depicts a resolution spoke type of resolution target at high resolution contrast (e.g. 100%), whereas FIG. 6B depicts a resolution spoke type of resolution target at low resolution contrast (e.g. 10%).

Figure 6C:
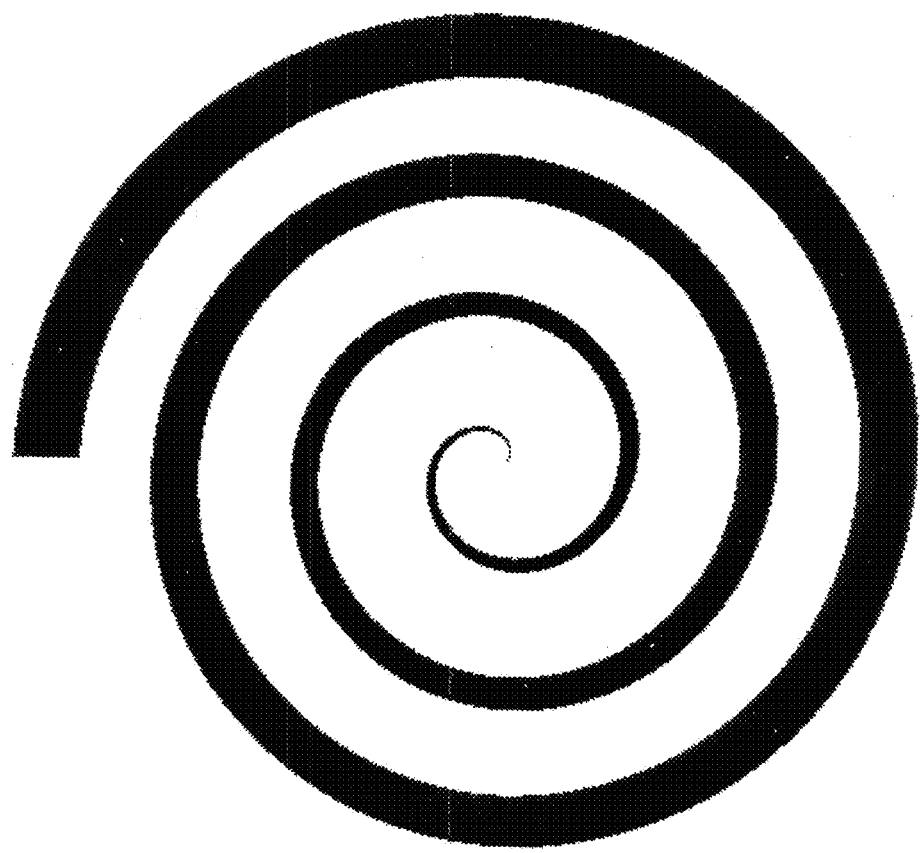
FIG. 6C depicts an Archimedes spiral type of resolution target at high resolution contrast.
Figure 6D:
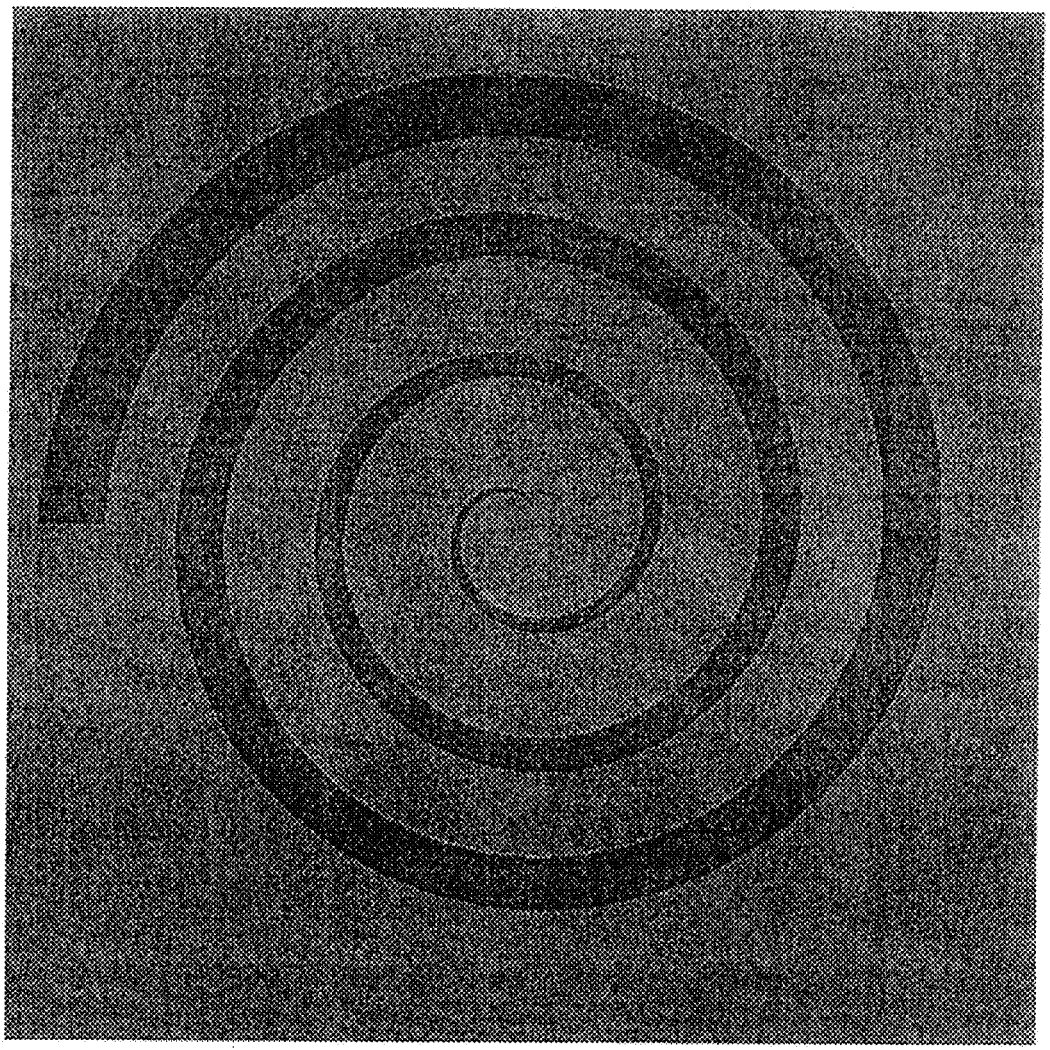
FIG. 6D depicts an Archimedes spiral type of resolution target at low resolution contrast.
Figure 16:
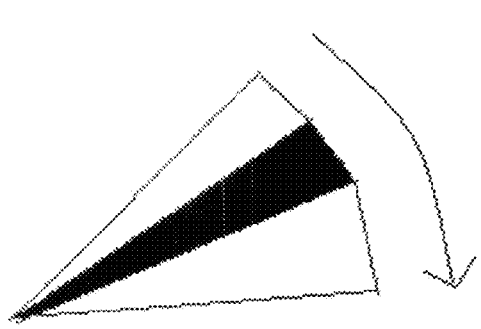
FIG. 16 depicts a schematic representation of tangential acuity.
Figure 17:
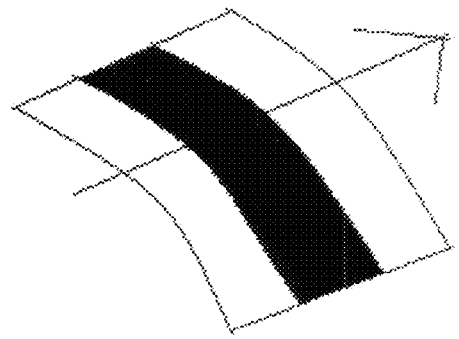
FIG. 17 illustrates a schematic representation of radial acuity.

It is possible that the resolution of the optical system can be changing in radial direction as well as in a tangential direction. As shown in FIG. 16, the tangential resolution or acuity can remain constant, as the radial resolution varies. Similarly, as shown in FIG. 17, the radial resolution or acuity can remain constant, as the tangential resolution varies. Relatedly, the vertical resolution may differ from horizontal resolution. A fifth resolution target technique involves the use of an Archimedes spiral, as shown in FIGS. 6C and 6D. With this approach, resolution in the radial direction can be evaluated, according to the desired resolution, in comparison to the resolution spoke, which can be used to evaluate resolution in the tangential direction.

For instance, when the spiral is to be used for very accurate, low aberration radial acuity testing, the spirals can be placed very closely to one another, creating a densely arranged target with many spirals from the inside to the outside. Relatedly, when the spiral is used for very accurate, low aberration radial acuity testing, the spirals can be make very thick. In terms of resolution contrast, FIG. 6C depicts an Archimedes spiral type of resolution target at high resolution contrast (e.g.

100%), whereas FIG. 6D depicts an Archimedes spiral type of resolution target at low resolution contrast (e.g. 10%).

A sixth approach involves a combination of a resolution spoke approach and an Archimedes spiral approach to obtain a real resolution measure. This approach is similar to combining two vectors, and can be represented by the following formula $$r=\sqrt{(r_1^2+r_2^2)}$$

where r denotes a real resolution, $r_1$ denotes a resolution estimate based on a resolution spoke approach, and $r_2$ denotes a resolution estimate based on an Archimedes spiral approach.

The resolution targets can also account for the contrast variation under similar acuity testing conditions. For instance, a 10% contrast acuity can be implemented by convolving a 10% contrast resolution target with a point spread function (PSF). FIGS. 5B, 6B, and 6D show the resolution target or resolution spoke at a low 10% contrast, whereas FIGS. 5A, 6A and 6C represent a high 100% contrast. Contrast can be defined as the difference in illumination between the maximum intensity and the minimum intensity, divided by the sum of the maximum intensity and the minimum intensity. Thus, contrast of the resolution target can be defined by the following formula.

$$\text{contrast}=(i_{max}-i_{min})/(i_{max}+i_{min})$$

Determining the Measure of Objective Optical Acuity of the Eye Based on the Image As noted above, a resolution target or a resolution target model can be convolved with a point spread function to produce a blurred image or a blurred image model. By evaluating the degree of blurring in the image, it is possible to determine the resolution of the optical system. For example, two resolution lines may be blurred to the extent that they are no longer discernable. On the other hand, the lines may be blurred yet still be discernable from each other. In the case of a convolved resolution spoke, there may be a certain resolution radius inside of which the spokes are not discernable, but outside of which the spokes are still discernable. Mathematical approaches can be used to determine what is discernable and what is not. Such determinations of discernability can be based on the analysis of intensity patterns of a resolution target, or models thereof, that have been convolved with a point spread function.

For example, the prediction or evaluation of optical acuity can be based on the analysis of the pixel values on a convolved dark area versus a light area. If the PSF is large enough, then it can convolve and blur the resolution spoke to a degree to which inside a circle having a certain radius, it is not possible to distinguish or discern between black and white areas. Yet outside of the circle, it is still possible to distinguish or discern the black and white areas. Accordingly, the radius of this circle can define the resolution of the optical system of the eye. As discussed below, it is possible to use Rayleigh's criterion to determine the appropriate resolution ring for determining the optical acuity of the optical system.

Resolution Determination

Determination of the optical resolution may be based on Rayleigh's criterion. For a diffraction-limited optical system with a circular aperture, operating in the absence of aberrations, the PSF can be represented by an Airy disk.

Figure 7:
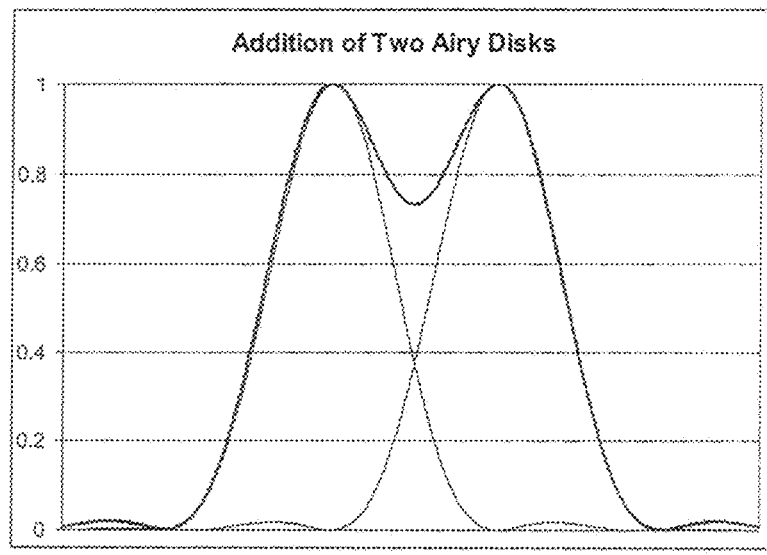
FIG. 7 shows a profile of two Airy disks.

According to the Rayleigh criterion, when two diffraction-limited point sources (Airy disks) are separated to a distance such that the first dark ring of one spot lies directly beneath the peak of the other spot, then the two spots can be considered to be discernable. The profile of the two added Airy discs is shown in FIG. 7, where the y-axis represents the normalized intensity, and the x-axis represents the spatial distance. These two Airy disks are separated by 1.22π radians. The profile of the addition of these two Airy disks can be written as $$i(r) = \left[\frac{2J_1(r)}{r}\right]^2 + \left[\frac{2J_1(r+1.22\pi)}{r+1.22\pi}\right]^2,$$

where i(r) is the intensity as a function of radius. As shown in the middle of the figure, the addition of the profiles results in two peaks and a valley therebetween. Solving this equation for the peak and valley gives a ratio of valley intensity to peak intensity of 0.7346 to 1. This contrast ratio represents the intensity contrast between the peak and the valley. According to this approach, if the contrast ratio of a resolution ring on a convolved resolution spoke is less than 0.7346, the resolution ring at that distance is considered to be discernable. In this way, the resolution determination can be based on Rayleigh's criterion. Results obtained from the Airy disk can form the basis for other approaches to determining discernability.

Figure 8A:
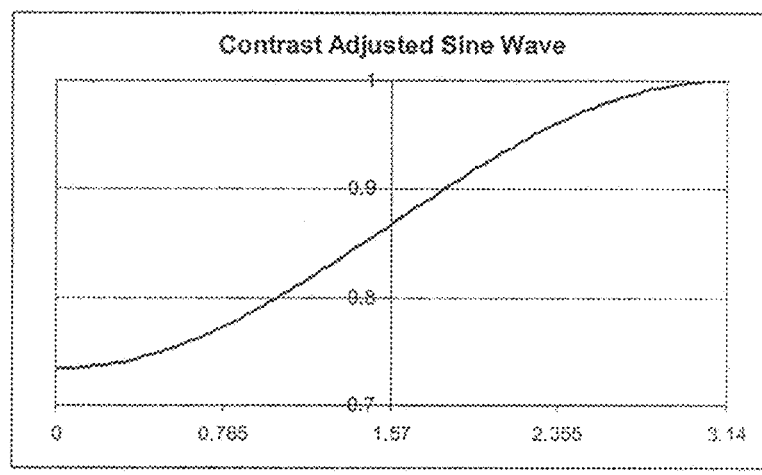
FIG. 8A illustrates a contrast adjusted sine wave.

Instead of using the Airy disk approach to determine what is discernable, it is possible to use a convolved resolution spoke image. A circle at a given radial distance from the center of a convolved spoke can produce a sinusoidal signal. When a contrast adjusted sinusoidal signal has 1 and 0.7346 as maximum and minimum intensity values, as shown in FIG. 8A, the expected ratio of averaged left quadrant to right quadrant can be expressed as $$\rho = \frac{\int_0^{\pi/2} [a_0 + b_0\cos(\theta + \pi/2)]d\theta}{\int_{\pi/2}^{\pi} [a_0 + b_0\cos(\theta + \pi/2)]d\theta} = a_0,$$

where $a_0=0.8673$ (average intensity value at left quadrant–dark) and $b_0=0.1327$ (average intensity value at right quadrant–light).

According to this approach, when two resolution spokes or lines are separated to a distance according to the Rayleigh's criterion, and if the contrast ratio of the darker portion (valley) to the brighter portion (peak) of the convolved spoke is smaller than 0.8673, then the two spokes or lines can be considered as discernable.

Figure 8B:
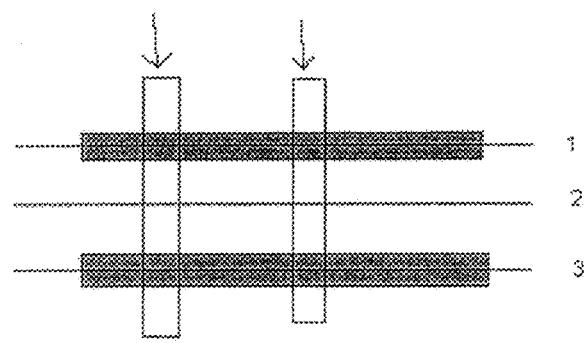
FIG. 8B illustrates two bars of a convolved resolution target of the plaid type.

In terms of bar lines, as shown in FIG. 8B, the determination can be based on the following formulas.

$$AverageBlack = \frac{\sum Pixel_1 + Pixel_3}{\sum L_1 + \sum L_3}, \text{ and}$$

$$AverageWhite = \frac{\sum Pixel_2}{\sum L_2}$$

where ΣPixel represents the sum of the intensity values of each pixel in the particular region of interest, and ΣL represents the actual number of pixels in the particular region of interest.

Thus, under the contrast adjusted sinusoidal approach, if $$\frac{AverageBlack}{AverageWhite}$$

is less than 0.8673, then the bars or lines are considered to be discernable. The formulation for discernable spokes follows a similar calculation.

Figure 8C:
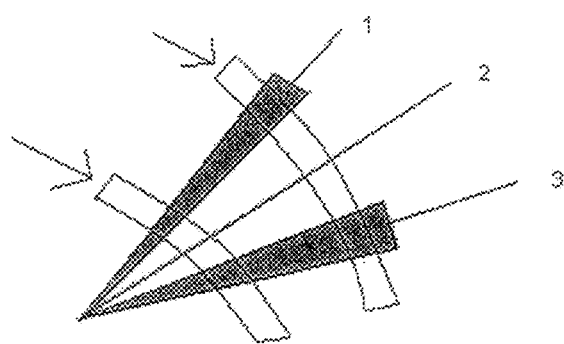
FIG. 8C illustrates two rays of a convolved resolution spoke.

FIG. 8B illustrates two bars of a convolved plaid type resolution target and FIG. 8C illustrates two rays of a convolved resolution spoke. As shown by the arrows in FIGS. 8B, it is possible to consider any portion along the length of the resolution bars, when calculating the contrast ratio. However, as illustrated by the arrows in FIG. 8C, with a resolution spoke the resolution can change along a radial direction. In other words, the contrast ratio at one resolution radius may be different from the contrast ratio at another resolution radius. Resolution rings located toward the center of the resolution spoke are less likely to provide a discernable contrast ratio, when compared to resolution rings toward the outer perimeter of the resolution spoke.

Calibration of Resolution Rings and Calculation of Acuity

The resolution rings can correspond to the radius at which the convolved resolution spokes remain discernable, and beyond which the spokes are no longer discernable. Determination of the resolution rings may depend on the angular spacing of the spokes and the contrast of the resolution target. As noted above, the Rayleigh criterion can be used to determine the smallest resolution ring that can still distinguish the resolution spoke, and thereby provide the resolution of the optical system. The resolution can then be converted to optical acuity in Snellen format as 20/20 plus number of letters, or in log MAR format, for example.

Several approaches can be used when determining and calibrating the resolution rings of a convolved resolution spoke. In a first approach, determination of the resolution ring can be accomplished using a 0.5 mm diameter pupil, or aperture size. The Airy disk radius can be calculated with the formula $r=1.22\lambda/D$, where $\lambda$ is the central wavelength of white light, and D is the diameter of the pupil. The disk radius in units of radians can be calculated in terms of arc minutes as $$r=1.22(0.55*180*60)/(0.5*1000*\pi)=4.613',$$

which corresponds to the radius of the first dark portion of the disk, where $\lambda$ is 0.55 μm. The ration $360/2\pi$ can be used to convert radians to degrees, and the ratio 60/1 can be used to convert degrees to arc minutes. This disk radius corresponds to about 33 pixels, when using a 512 frame size. Different frame sizes may have different calibration factors.

Based on these calculations, 1' (one arc minute) is equal to 33/4.613, or about 7.153 pixels. In this first approach, the resolution is pupil size dependent. The arc length of each spoke at a normalized radius can be calculated with the following formula.

$$\text{arc length}=2\pi r/\theta=360°r/x°$$

Thus, $$x/(360*2\pi*256 \text{ pixels}*r)=7.153 \text{ pixels (for 20/20);}$$
and $$r=(7.153*360)/(2\pi x*256)=0.1067$$

Consequently, the resolution radius for 20/20 acuity is determined to be 0.1067. Table 1 illustrates the various resolution radius values corresponding to the Snellen acuity values, based on this first approach to calibrating the resolution rings.

TABLE 1

| | Acuity | | | | |
|---|---|---|---|---|---|
| | 20/10 | 20/20 | 20/40 | 20/80 | 20/160 |
| r | 0.053 | 0.1067 | 0.213 | 0.427 | 0.854 |

Table 1 corresponds to the resolution rings shown in FIGS. 10A-E, where different resolution radius values correspond to different optical acuity measure. Other approaches can be used to calibrate the resolution rings based on this first approach.

For example, a second approach to calibration of the resolution rings involves introducing a small amount of focusing error to the resolution spoke to observe the effect of contrast reversal. Contrast reversal refers to the phenomenon where the appearance of a single spoke alternates between dark and light, as seen in FIGS. 9A and 9B. FIG. 9A shows the contrast reversal with 0.25D focusing error for a 6 mm pupil with 6° spacing in the resolution spoke. FIG. 9B shows the contrast reversal with 0.25D focusing error for a 6 mm pupil with 10° spacing in the resolution spoke. FIG. 9C shows an optical transfer function of the defocused resolution image of FIG. 6B. As illustrated in FIGS. 9B and 9C, the 4 contrast reversals correspond to four places where the optical transfer function (OTF) changes sign.

With contrast reversal, it is possible to construct a resolution spoke and convolve it with only a small amount of defocus. With the second approach, on average, the real r is about 0.4 times as small as expected when compared to the first approach. That means the resolution ring radius r from the first approach can be scaled by a factor of about 0.4 to arrive at the resolution ring radius as derived by the second approach, as shown by the following formula which can estimate the resolution ring radius according to the second approach.

$$r=(7.153*0.4*360)/2\pi x*256 \quad \text{(modified formula)}$$

The second column of Table 2 lists the spatial frequencies of the four sign reversals N in the optical transfer function (OTF) after diffraction-limited OTF calibration as shown in FIG. 6C. The spatial frequency can be expressed in terms of cycles per degree, and can be used as a measure of resolution. The spatial frequencies of the second column can be used to calculate the arc minute values of the third column, according the following formula $$x=30/f$$

where x denotes arc minutes, and f denotes spatial frequency. Typically, 20/20 acuity correlates to 30 cycles per degree, which also corresponds to one arc minute.

The fourth column contains resolution ring radius calculations based on the modified formula as noted above, as calculated from the optical transfer function. This calculation involves considering the pupil size as 1, and normalizing the resolution ring radius. The fifth column contains resolution rings radius estimates based on visual inspection of the contrast reversal in the resolution spoke as shown in FIG. 6B. The fifth column is the ratio of the ring at reversal, versus the overall size of the resolution target.

TABLE 2

| N | Freq (cpd) | Arc minute | r | real |
|---|---|---|---|---|
| 1 | 23.0 (+ to −) | 0.767 | 0.102 | 0.06 |
| 2 | 33.5 (− to +) | 1.12 | 0.156 | 0.16 |

TABLE 2-continued

| N | Freq (cpd) | Arc minute | r | real |
|---|---|---|---|---|
| 3 | 54.5 (+ to −) | 1.82 | 0.273 | 0.27 |
| 4 | 101.6 (− to +) | 3.39 | 0.391 | 0.40 |

Table 2. Spatial frequencies during sign reversal in the optical transfer function (OTF) corresponding to the radius of the resolution rings at the contrast reversal in the resolution spoke.

A third approach to calibration involves using different pupil sizes to construct different point spread functions (PSFs) to determine the resolution radius r of the individual pupil sizes. This approach can be based on a diffraction limited case having no wavefront aberration. Table 3 shows the calculated resolution radius r corresponding to various pupil sizes. Here, the scaling factor is 0.6 as compared to the first approach.

TABLE 3

(diffraction limited case)

| No. | pupil | Airy disk | resolution r | ratio | ratio/0.1067 |
|---|---|---|---|---|---|
| 1 | 0.25 mm | 9.226' | 0.58 | 0.063 | 0.59 |
| 2 | 0 5 mm | 4.613' | 0.28 | 0.061 | 0.57 |
| 3 | 1 mm | 2.306' | 0.14 | 0.061 | 0.57 |
| 4 | 2 mm | 1.153' | 0.06 | 0.052 | 0.49 |

Figure 19:
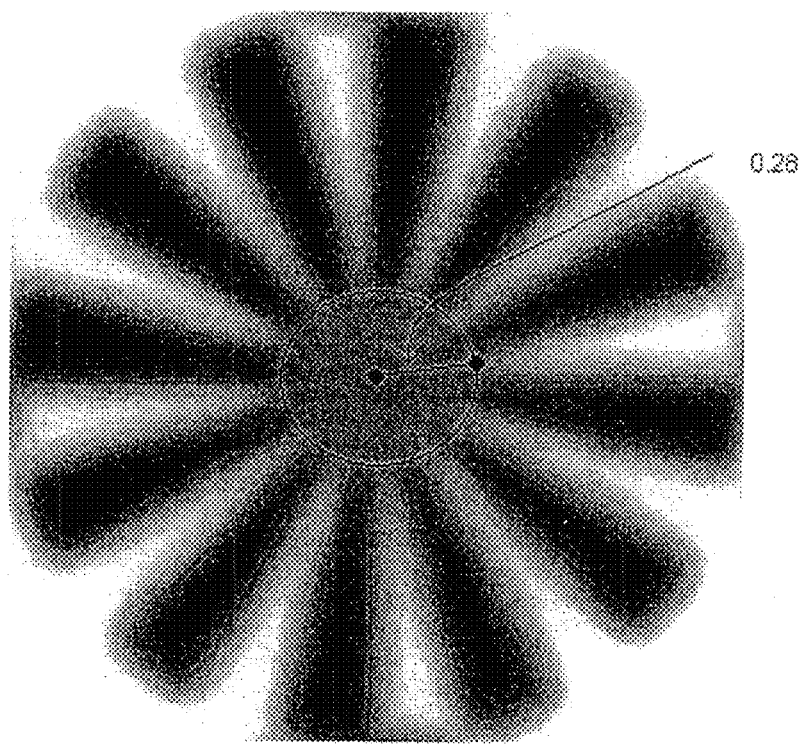
FIG. 19 shows a convolved resolution spoke.

The Airy disk radius of the third column, in terms of arc minutes, can be calculated from the second column according to the formula $r=1.22\lambda/D$, where D is the pupil diameter. The resolution r of the fourth column can be based on a visual inspection of the convolved target. For example, as shown in FIG. 19, and described in the second row in Table 3, for a 0.5 mm pupil, the resolution radius r is estimated at 0.28. The ratio of the fifth column can be calculated by dividing the resolution r of the fourth column by the radius of the Airy disk as indicated in the third column. This ratio can divided by 0.1067, which is the resolution radius at 20/20 Snellen acuity, as noted above in Table 3, and the result is shown in the sixth column. The calibration factor can then be based on the values in the sixth column, which are approximately 0.6.

It may be desirable to average of 0.4 from the second approach, and 0.6 from the third approach, to arrive at a calibration factor of 0.5. Hence, the resolution radius can be calculated as $$r=(7.153*0.5*360)/(2\pi x*256)=(7.153*360)/(2\pi y*256)$$

where $y=2x$ is the spacing factor. In this case, $y=30$, so $r=0.05336$, which is about one half the originally estimated value of 0.1067.

Figure 10A:
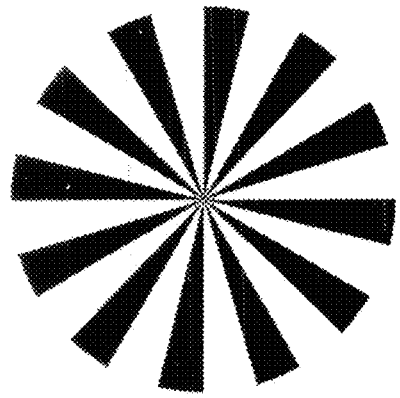
FIG. 10A illustrates a resolution spoke having a resolution ring corresponding to an optical acuity of 20/10.
Figure 10B:
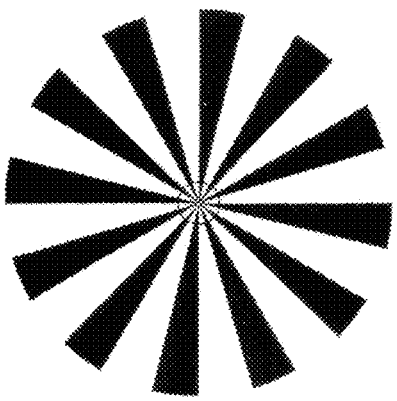
FIG. 10B illustrates a resolution spoke having a resolution ring corresponding to an optical acuity of 20/20.
Figure 10C:
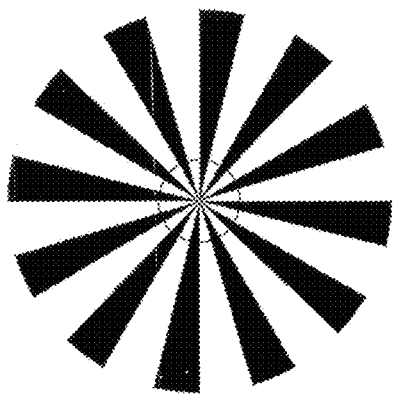
FIG. 10C illustrates a resolution spoke having a resolution ring corresponding to an optical acuity of 20/40.
Figure 10D:
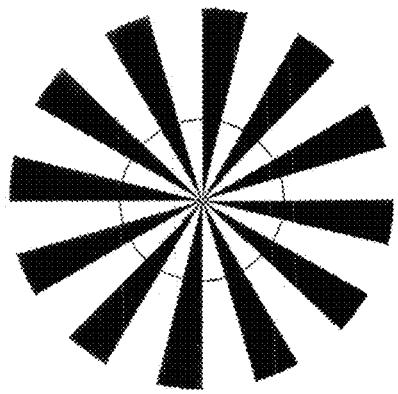
FIG. 10D illustrates a resolution spoke having a resolution ring corresponding to an optical acuity of 20/80.
Figure 10E:
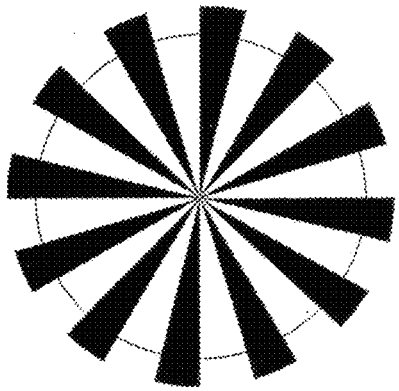
FIG. 10E illustrates a resolution spoke having a resolution ring corresponding to an optical acuity of 20/160.

After the calibration, the resolution ring for a particular resolution spoke (15° spacing) is shown in FIGS. 10A-E. FIG. 10A illustrates a resolution spoke having a resolution ring corresponding to an optical acuity of 20/10. FIGS. 10B-10E illustrate resolution spokes having resolution rings corresponding to optical acuities of 20/20, 20/40, 20/80, and 20/160 respectively. Therefore, the radius of the resolution ring for 20/20 acuity can be represented by the following general formula.

$$r = \frac{360m}{4\pi xd},$$

where m is the pixel resolution per arc minute for the diffraction-limited PSF, x is the spoke spacing in degrees and d is the total number of pixels of the image frame. The image frame here is 512×512 pixels. The resolution spoke, the PSF, and the convolved image can all have a frame dimension of 512×512 pixels.

Typically, a larger pupil will have a smaller point spread function, and vice versa. For example, if the pupil diameter is less than 2 mm, the diffraction limited point spread function may already be large enough, and there may be less need for corrective surgery. For eyes having larger pupils, higher order aberrations may play a greater role.

Figure 13:
FIG. 13 shows a convolved Archimedes spiral resolution target.

FIG. 13 shows a convolved Archimedes spiral resolution target. Calculation of optical acuity can be based on the same principles discussed above with respect to resolution spokes. Higher resolution measures correspond to resolution rings located toward the inner areas of the spiral, whereas lower resolution measures correspond to resolution rings located toward the outer periphery of the spiral.

Figure 14:
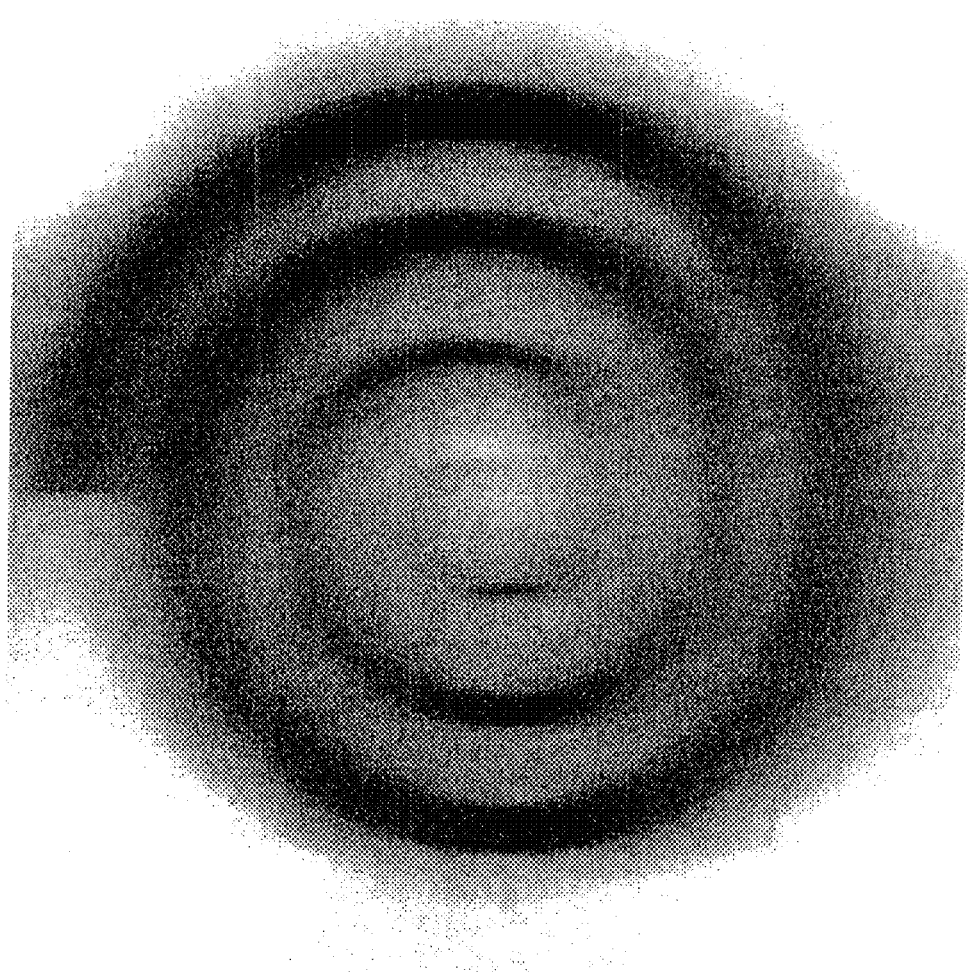
FIG. 14 depicts a convolved Archimedes spiral resolution target.

It will be appreciated that the PSF may not always be rotationally symmetric, as is possible in cases of astigmatism or coma. In some instances, it may be desirable to do averaging or a combination method based on vectors provided by a resolution spoke approach and an Archimedes spiral approach, as discussed above. Similarly, some eyes may have strong horizontal astigmatism, and the vertical acuity may be better than the horizontal acuity. By using resolution targets such as Archimedes spiral, it may be possible to capture the directional bias, as shown in FIG. 14.

FIGS. 16 and 17 illustrate tangential acuity and radial acuity, which are further explained in Table 4.

TABLE 4

| Direction | Acuity/Resolution Measure |
|---|---|
| concentric/circular | tangential/torsional |
| inward - outward | radial |

Figure 18:
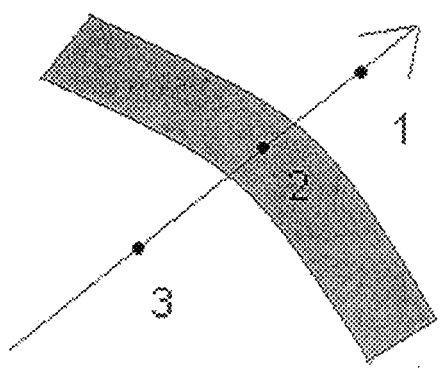
FIG. 18 illustrates a segment of a convolved Archimedes spiral.

As shown in FIG. 18, the acuity evaluation methods discussed above in reference to resolution spokes can also be applied to Archimedes spiral, including pixel calculations and the like. Multiple wavefront measurements may also provide benefits.

Readjustment for Centration

As discussed above, after the resolution spoke is convolved with the point spread function (PSF), and the resolution rings are determined, Rayleigh's criterion can be implemented to determine the optical acuity. Ideally, the point spread function will be exactly centered with respect to the center of the spoke, thus making determination of optical acuity a more straightforward process. In some cases, however, the point spread function (PSF) may not be centered. In fact, certain Zernike polynomial terms have an x- or y-component. Accordingly, the point spread function (PSF) for certain eyes may have some degree of de-centration. This de-centration can dramatically affect the estimated optical acuity. Therefore, it may be desirable to re-center the point spread function. To readjust for centration, the following four approaches can be used. Two approaches involve the pupil plane, and two involve the imaging plane.

In a first centration approach involving the pupil plane, the average wavefront tilt is calculated and then compensated for the tilt. This approach can be implemented with the Zernike derivative or with the discrete wavefront differential averages.

Denoting $Z(r,\theta)$ as Zernike polynomials, the derivative of the wavefront $W(r,\theta)$ can be written as $$\frac{\partial W(r,\theta)}{\partial x} = \frac{\partial}{\partial x}\sum_{i=1}^{N} c_i Z_i(r,\theta) = \sum_{i=1}^{N} c_i \frac{\partial Z_i(r,\theta)}{\partial x}$$

$$\frac{\partial W(r,\theta)}{\partial y} = \frac{\partial}{\partial y}\sum_{i=1}^{N} c_i Z_i(r,\theta) = \sum_{i=1}^{N} c_i \frac{\partial Z_i(r,\theta)}{\partial y}$$

where the Zernike derivative can be derived analytically so that the average wavefront tilt in both x- and y-directions can be calculated.

In a second centration approach involving the pupil plane, the wavefront derivative can be implemented as the average wavefront pixel difference between two neighboring pixels in either x- or y-direction, as shown in the following equations.

$$\frac{\partial W(r,\theta)}{\partial x} = \frac{1}{n}\sum_i\sum_j (W_{i,j+1} - W_{i,j}), (r \leq 1)$$

$$\frac{\partial W(r,\theta)}{\partial y} = \frac{1}{n}\sum_i\sum_j (W_{i+1,j} - W_{i,j}), (r \leq 1)$$

The calculation can be done within the pupil area with n the total number of pixels within the area.

A first imaging plane approach is based on the calculated center of gravity of the point spread function (PSF). The center of gravity of PSF can be implemented according to the following equation:

$$a_x = \frac{\iint xi(x,y)dxdy}{\iint i(x,y)dxdy} = \frac{\sum_i\sum_j jI_{i,j}}{\sum_i\sum_j I_{i,j}}$$

$$a_y = \frac{\iint yi(x,y)dxdy}{\iint i(x,y)dxdy} = \frac{\sum_i\sum_j iI_{i,j}}{\sum_i\sum_j I_{i,j}}$$

where $i(x,y)$ and $I_{i,j}$ represents the point spread function in functional and discrete representations, respectively. This approach can also be referred to as pixel weighting.

In a second imaging plane approach, a blurred spoke, for example, can be cross correlated with an input spoke. The cross correlation between the shifted blurred spoke and the input resolution spoke can be expressed as $$c(a_x,a_y) = I(x,y) \oplus i(x-a_x, y-a_y),$$

where $I(x,y)$ denotes the input resolution spoke, $i(x,y)$ denotes the blurred resolution spoke, and $\oplus$ denotes a symbol for correlation. The correlation function can provide an indication to what degree the blurred image is de-centered relative to the input image. A surface search for the maximum value in the correlation function $c(a_x,a_y)$ can give the needed re-centration shift. For example, a function having 100×100 pixels provides a total of 10,000 pixel values. A surface search can determine the position of the highest or maximum value pixel among these. Accordingly, this approach can have one pixel accuracy.

Once the image shift is obtained, it is possible to implement the adjustment. A first way of implementing the adjustment is to shift the point spread function (PSF) directly. If the point spread function (PSF) is fairly spread, this approach may require necessary data discard and zero padding. A second way of implementing the adjustment is to modify the wavefront tilts in the pupil plane to achieve the eventual shift in the blurred resolution spoke. Once the centration is readjusted, the point spread function can be centered and the estimation of the optical acuity can be reliable. FIGS. 11A and 11B shows a blurred resolution spoke without and with centration readjustment, respectively. Re-centration adjustment appears to result in a sharper image. The estimated optical quality for FIG. 11A is 0.87 log MAR, whereas the estimated optical quality for FIG. 11B is 0.48 log MAR.

Clinical Test Results

To test the effectiveness of this technique, the following four clinical test results may be useful for prediction: high contrast uncorrected visual acuity, low contrast uncorrected visual acuity, high contrast best spectacle corrected visual acuity, and low contrast best spectacle corrected visual acuity.

Wavefront measurements were taken from eleven eyes at one-year post surgery from patients undergoing myopic LASIK surgery. Optical acuity measures for these eyes were predicted according the present invention. The predicted visual acuity is compared to the corresponding subjective measurements with 100% contrast. FIG. 12 shows the correlation of the measured UCLM versus the predicted UCLM for these eyes. The predicted UCLM is an average of predicted UCLM from typically 3 to 5 wavefront measurements, with the standard deviation also shown in the figure. The correlation variance between predicted and measured was observed to be about 74%. Hence, for the first time the optical acuity of human eyes can be accurately measured objectively.

Many of these wavefronts were taken in a dim ambient lighting condition, where a pupil diameter may be, for example, about 6 mm. In contrast, a visual acuity test usually is done in a slightly brighter lighting condition, where a pupil diameter may be, for example, about 4.5 mm. Therefore, these results may reflect some discrepancy between the predicted acuity and the measured acuity. Though this can be compensated for, it may be desirable to know the exact pupil size when the visual acuity test is taken. Based on this knowledge, the input wavefront map can be truncated to approximate the pupil size of the eye that underwent visual acuity testing, thereby permitting a direct comparison, and allowing an accurate prediction or determination of optical acuity. Thus, a 6 mm pupil diameter could be truncated, and a 4.5 mm wavefront portion could form the basis of the point spread function, and the subsequent acuity evaluation method.

Figure 15A:
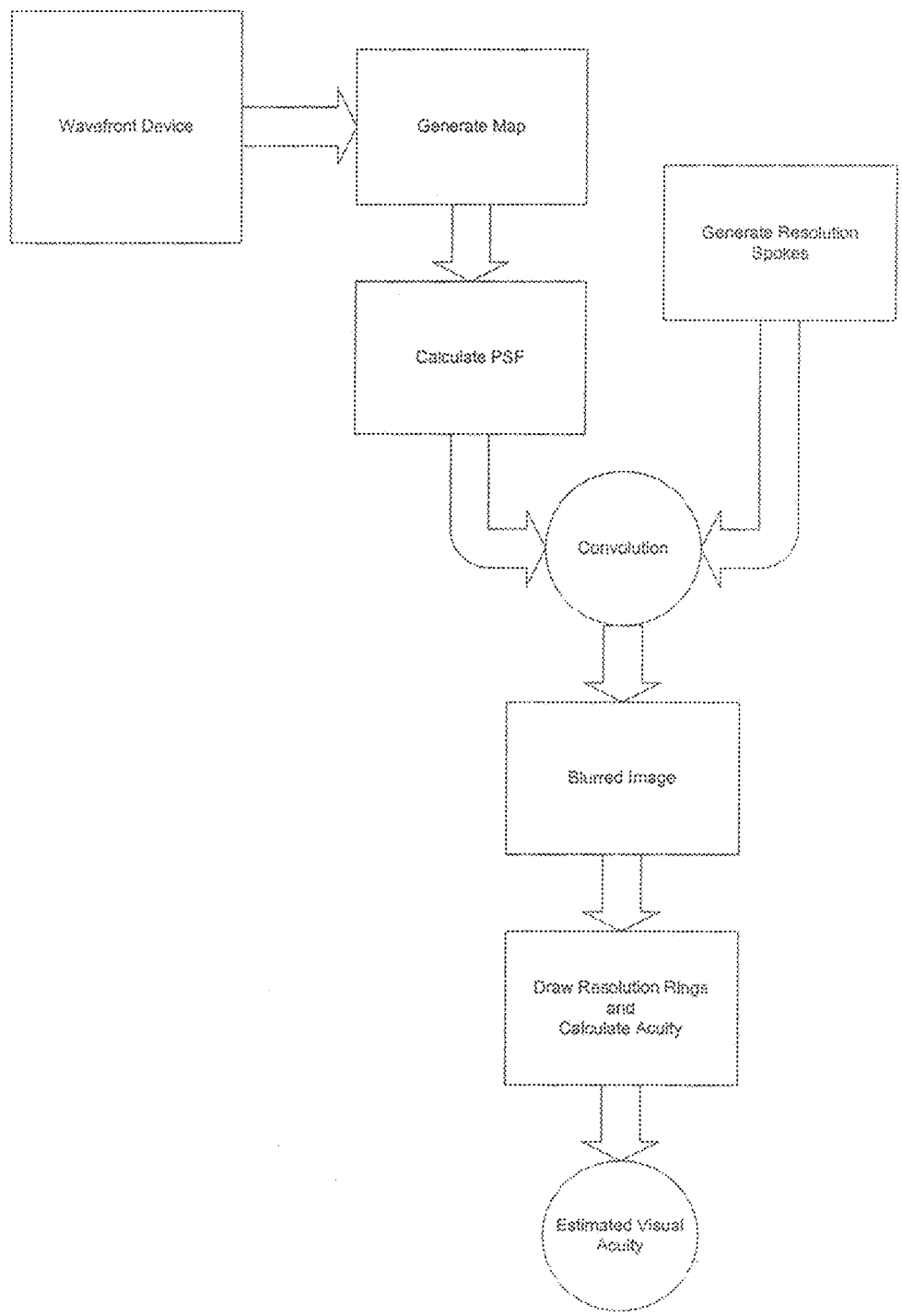
FIG. 15A shows a procedural flowchart.
Figure 15B:
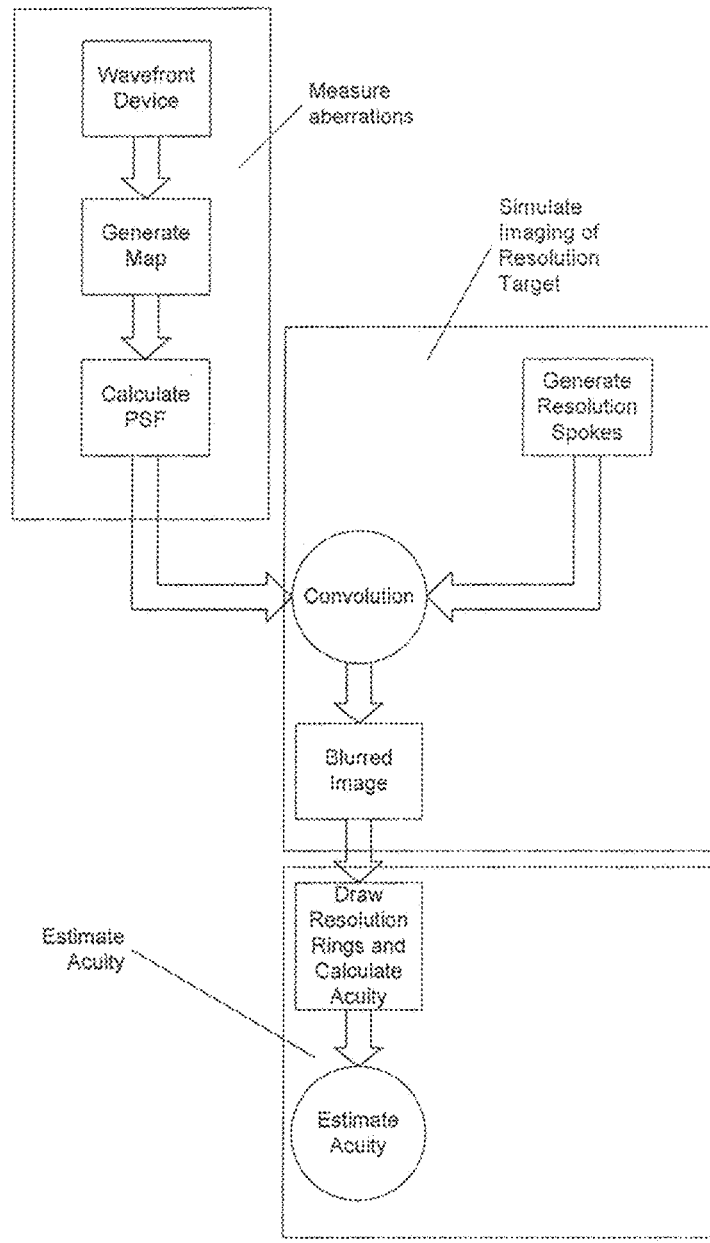
FIG. 15B shows a system diagram.
Figure 15C:
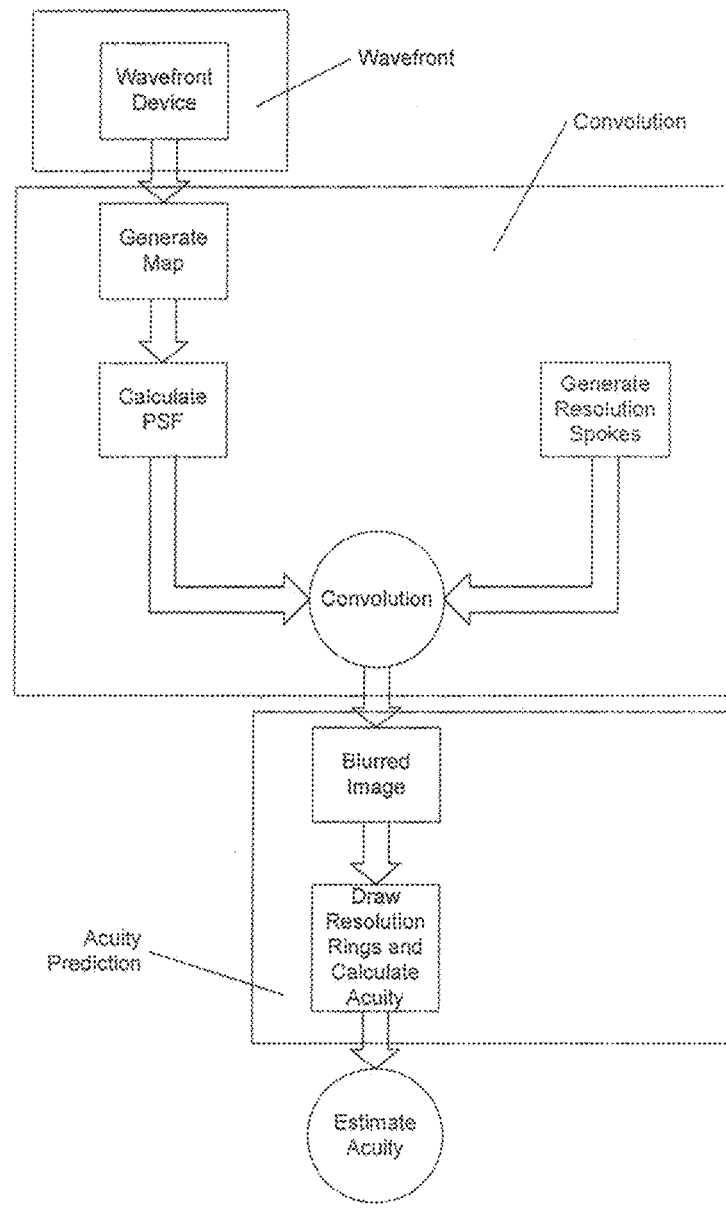
FIG. 15C shows a system diagram.
Figure 15D:
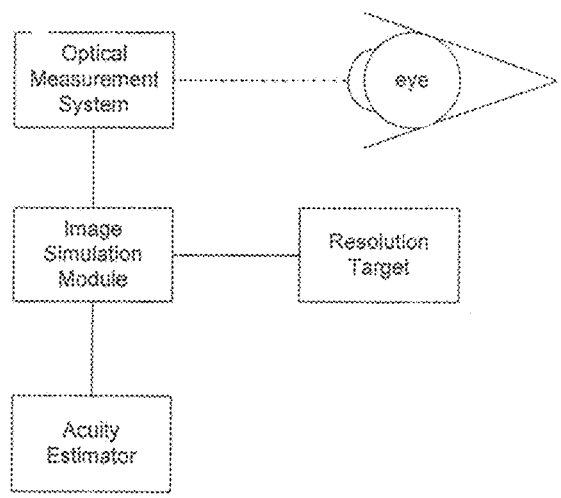
FIG. 15D shows a system diagram.
Figure 15E:
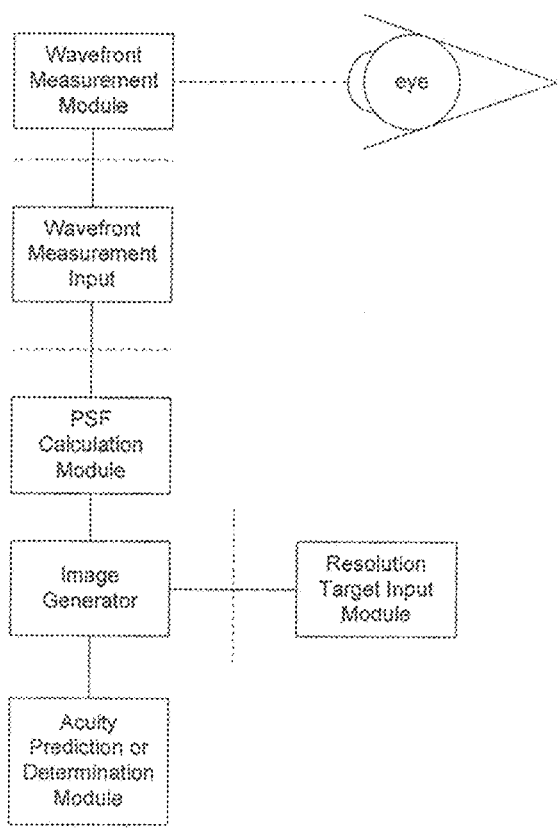
FIG. 15E shows a system diagram.

The present invention also provides systems for predicting an optical acuity measure of an eye, as depicted in the procedural flowchart of FIG. 15A, and related system diagrams of FIGS. 15B-E. As shown in FIG. 15B, a system of the present invention can include a module that measures aberrations, which can include a wavefront measurement submodule, a wavefront map submodule, and a point spread function submodule. The system can also include a module that simulates imaging of a resolution target, and this module can include a resolution target submodule, a convolution submodule, and an image submodule. The system can further include an acuity evaluation module, which can include acuity calculation and prediction submodules. FIG. 15C illustrates that a system of the present invention can include a wavefront module, a convolution module that can have a wavefront map submodule, a point spread function submodule, a resolution target submodule, and a convolution submodule. The system can also include an acuity evaluation module that can have an image submodule and an acuity submodule. As depicted in FIG. 15D, a system according to the present invention can include an optical measurement module, an image simulation module that accepts a resolution target, and an acuity estimator module. FIG. 15E illustrates that a system of the present invention can include a point spread function module, an image module, and an acuity module. The system may also include a resolution target input module. The system may have a wavefront measurement input module, and the system may have a wavefront measurement module.

A system according to the present invention can have a module that determines a point spread function based on a wavefront measurement of an eye, a module that convolves a resolution target with the point spread function to produce an image, and a module that predicts the optical acuity measure of the eye based on the image. The system can also include an input that accepts the wavefront measurement of the eye, as well as a module that determines the wavefront measurement of the eye.

Similarly, the present invention provides for a system that includes a module that measures visual distortion induced by optical aberrations of an eye of an individual to determine an imaging performance of the eye, a module that constructs an acuity measurement model by simulating imaging performance of the eye for a resolution target, and a module that determines an estimated visual acuity of the eye using the acuity measurement model. The module that determines an estimated visual acuity may operate such that the estimated acuity accurately correlates to an actual visual acuity of the eye.

Evaluation Output

The approaches of the present invention also provide for the generation of an evaluation output for one or more eyes. An evaluation output may also be used to make a prediction of the outcome of an optical treatment procedure before the treatment is administered, or to evaluate the outcome of an optical treatment procedure after the treatment is administered.

In one embodiment, the evaluation output includes a visual acuity prediction for the eye. For example, Zernike polynomials from a wavefront exam can be read into a StringGrid object and calculation of a point spread function can be performed. An aperture, if smaller than the pupil size, can also be used to take the effect of pupil shrinkage. This approach can be used to mitigate presbyopia, as further discussed in U.S. Provisional Patent Application No. 60/579,124, filed Jun. 10, 2004 (Attorney Docket No. 018158-022230US), the entire contents of which are incorporated herein by reference. Nine eye chart letters (C, D, E, F, L, O, P, T, and Z) can be generated with fixed size corresponding to different visual acuity targets from 20/10 to 20/100 (e.g. 20/10, 20/12, 20/15, 20/20, 20/25, 20/32, 20/40, 20/50, 20/64, 20/80, and 20/100). By selecting a combination of an eye chart letter and a visual acuity target, this approach can perform a convolution of the PSF calculated from the current wavefront exam with the selected eye chart letter. By visually determining whether the convolved letter is discernable it is possible to predict a visual acuity for the eye based on the current exam.

Aberrations

The present invention also provides for the correlation between optical aberrations and visual acuity, such that it is possible to determine or identify those aberrations which contribute to bad vision, those aberrations which contribute to good vision, and those aberrations which do not affect vision. Such determinations can be useful in designing ablation profiles that induce aberrations where there were none, modifying existing aberrations, and/or deliberately not treating some aberrations that may contribute to good vision, wherein the aberrations can include high order aberrations, for treating a vision condition in a patient. Such approaches can be used, for example to design a treatment shape for presbyopia, based on the teachings found in U.S. Pat. Nos. 6,280,435 and 6,663,619 to Odrich et al. (Attorney Docket Nos. 018158-011110US and 018158-011120US), and U.S. Provisional Patent Application No. 60/579,124, filed Jun. 10, 2004 (Attorney Docket No. 018158-022230US), the entire contents of which are incorporated herein by reference.

Point Spread Function Evaluation and Centration

Figure 20:
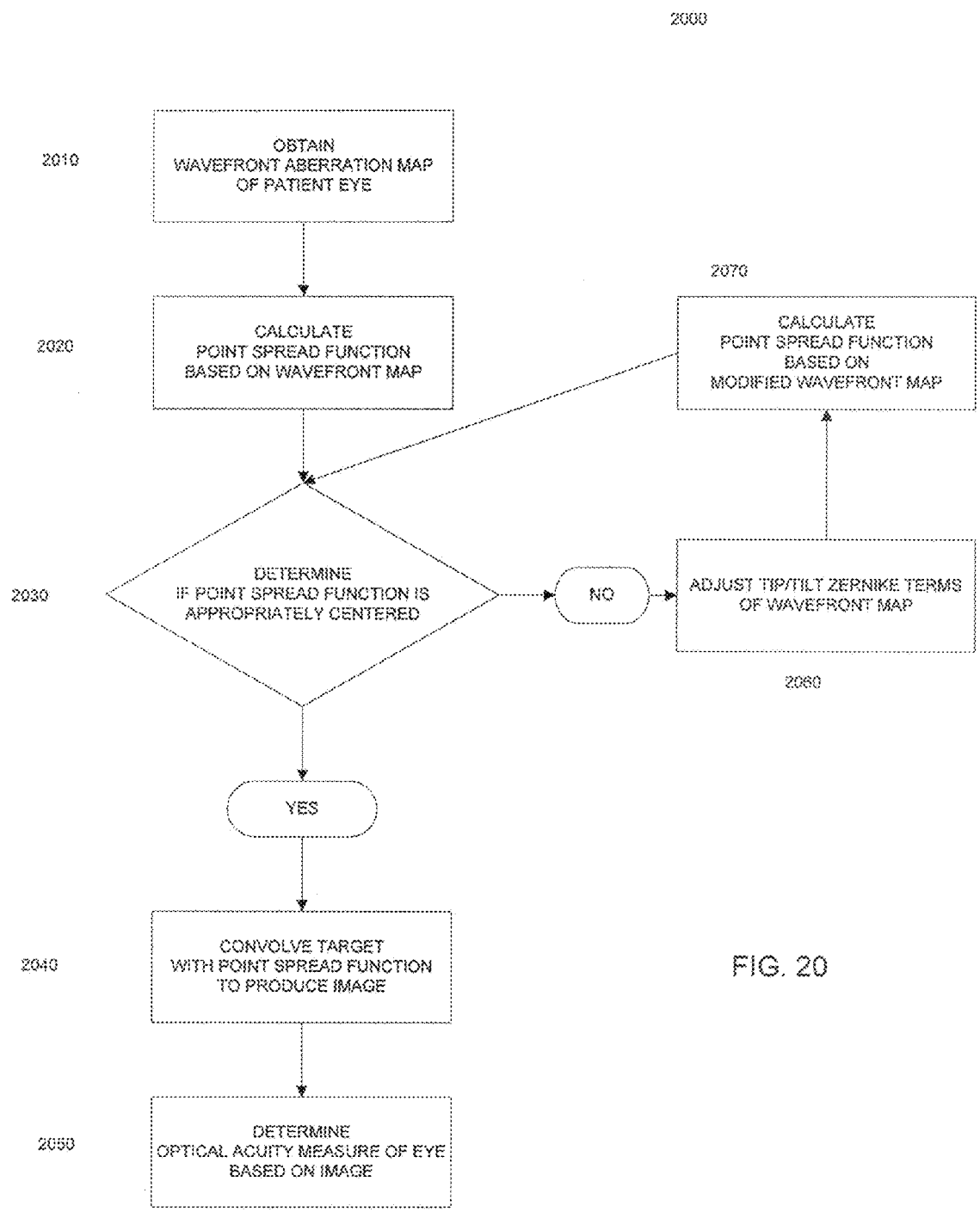
FIG. 20 depicts aspects of a method for determining an optical acuity measure of an eye according to embodiments of the present invention.

Embodiments of the present invention encompass systems and methods that involve centering a point spread function for use in vision simulation and acuity evaluation techniques. As shown in FIG. 20, an exemplary method 2000 may include obtaining a wavefront aberration map of a patient eye (step 2010), calculating a point spread function based on the wavefront map (step 2020), and determining whether the point spread function is appropriately centered (step 2030). If it is determined that the point spread function is appropriately centered, the method may include convolving a target with the point spread function to produce an image (step 2040), and determining an optical acuity measure of the eye based on the image (step 2050). If, on the other hand, it is determined that the point spread function is not appropriately centered, the method may include adjusting tip and/or tilt terms of the wavefront aberration map (step 2060), calculating a point spread function (step 2070) based on the adjusted wavefront map, and determining whether the subsequent point spread function is appropriately centered (step 2030). The process (e.g. steps 2060, 2070, and 2030) may be repeated until an appropriately centered point spread function is calculated.

In some instances, the procedure of determining whether a point spread function is appropriately centered involves one or more iterations through steps 2020, 2030, and 2060. For example, this process can be repeated until a pre-determined metric is met, thus indicating that the point spread function is appropriately centered. In many cases, just one iteration may be sufficient. In other cases, it may require a couple of more iterations to meet the pre-determined metric, for example if a large portion of the original point spread function is out of the field. An exemplary pre-determined metric may be within a range from about 0.1 microns to about 10 microns. For example, a value of 0.1 microns, 1 micron, or 10 microns may be used for the metric. The pre-determined metric can be based on the distance from the center of the point spread function to the center of the frame. According to some embodiments, the dimensions of the frame size are selected as odd numbers (e.g. 101×101), and hence the frame center is at (0, 0), or the origin of the coordinates.

For some point spread function calculations, the field of view may be too large, and the details of the point spread function cannot be seen. Frequently, it may be desirable to pad zeros outside the ocular wavefront. Suppose we pad zeros so the original wavefront of a frame size n×n becomes an xa×n. After the calculation, it is possible to cut the point spread function frame to exactly the original size of n×n. In this case, the field of view v of the point spread function is determined by the equation $$v = \frac{10.8n\lambda_0}{\pi\alpha D}.$$

Here, $\lambda_0$ is in μm and D is in mm to get v in arc minute. To convolve the point spread function with a vision target, such as an eye chart or a scene, with a frame size of M×N, it is possible to determine the field of view of the entire target $V_m \times V_n$ by means of certain facts. For example, where letters on the 20/20 line have a height of 5 arc minutes, if each letter spans 12 pixels, a 480×600 pixels eye chart spans 200'×250'. When convolving a point spread function from an ocular wavefront with a target, it is helpful to match the pixel resolution of the two frames, pursuant to the equation $$\frac{v}{n} = \frac{10.8\lambda_0}{\pi\alpha D} = \frac{V_m}{M} = \frac{V_n}{N}.$$

The above equation indicates that the point spread function frame and the target frame have the same pixel resolution, and the pixel resolutions in both the horizontal and the vertical directions are the same. Hence, when the target image is resized, the aspect ratio is also be kept. As an exemplary illustration, consider an image of an ETDRS eye chart of size 2449×2991 pixels. The height of a letter E on a 20/160 line is measured to be 350 pixels. It is possible to calculate the field of view and the pixel resolution of the eye chart, and to design an ocular wavefront so a convolution can be performed for a 5 mm pupil. Because the height of a 20/20 letter spans 5 arc minutes, the height of a 20/160 letter spans 8×5=40 arc minutes. Therefore, the pixel resolution of the eye chart is 40/350=0.1143 arc minute/pixel. Hence, the field of view of the eye chart is 2449·0.1143'×2991·0.1143'=278.2'×339.8', or 4.6°×5.7°. Again from the above equation, it is possible to obtain α=10.8×0.55/(0.1143×5π)=3.3084. This may not be preferred, because α may be better as an integer. A solution is to resize the target so α=3. To do so, the above equation can be used to provide the new pixel resolution as v/n=10.8×0.55/(3π×5)=0.126, or the target is 0.126/0.1143=1.1024 times as small. This indicates that the original target is resized to 2449/1.1024×2991/1.1024=2222×2713. Since the field of view won't change after the resizing, the pixel resolution becomes larger as M and N decrease. For the ocular wavefront, there is a greater freedom. Consider the case where 100×100 is the wavefront frame size, and the point spread function has a field of view v=100×0.126'=12.6'. If a smaller field of view is desired in order to see more details of the point spread function, the frame size will be reduced. For example, for a 60×60 field of view for the point spread function, the wavefront frame size will be 6/0.126=48 or 48×48.

According to some embodiments, the extent to which a point spread function is decentered, or a centration measure of the point spread function, can be determined by method 2100 as illustrated in FIG. 21. As shown here, method 2100 includes calculating a diffraction limited point spread function (step 2110), obtaining a wavefront aberration map of the patient eye (step 2120), and calculating a point spread function based on the wavefront map (step 2130).

In some cases, the diffraction limited point spread function can be calculated with the same parameters used for the regular point spread function, for example using the same formula, the same frame size, the same scaling, the same pupil size, and the same point spread function model (e.g. monochromatic or polychromatic). The difference is that calculation of the diffraction limited point spread function (step 2110) uses a zero wavefront aberration, whereas calculation of the regular point spread function (step 2130) uses an actual wavefront aberration. Method 2100 further includes correlating the point spread function with the diffraction limited point spread function (step 2140). For example, a 2-D correlation can be performed on the point spread function with the diffraction limited point spread function to obtain a correlation matrix R. The size of correlation matrix typically matches the frame size. Hence, for a point spread function frame size of 101×101, the size of matrix R is 101×101.

Method 2100 may also include searching for or identifying the maximum value pixel in the correlation matrix (step 2150). Typically, the maximum value pixel represents the center of the point spread function. As shown here, the method can also include obtaining a sub-pixel resolution (step 2160). In some instances, the sub-pixel resolution can be calculated by obtaining the eight pixels surrounding the maximum value pixel, and performing the following calculation.

$$I = [R_{i-1,j-1}(-1) + R_{i-1,j}(-1) + R_{i-1,j+1}(-1) + R_{i+1,j-1} + R_{i+1,j} + R_{i+1,j+1}]/(9R_{i,j}) + i$$

$$J = [R_{i-1,j-1}(-1) + R_{i,j-1}(-1) + R_{i+1,j-1}(-1) + R_{i-1,j+1} + R_{i,j+1} + R_{i+1,j+1}]/(9R_{i,j}) + j$$

Here, (i,j) represents the matrix indices of the maximum value pixel of correlation matrix R, and can be expressed in terms of integers or pixels. (I, J) stands for the actual positions at the image plane and can be expressed in terms of non-integer values or real numbers. If the maximum value pixel is at the edge, more iterations may be needed to bring the point spread function toward the center. Evaluation of the center of the point spread function or the approximation thereof can be used to determine if the point spread function is appropriately centered (step 2170). In some instances, a first iteration may provide a sub-pixel resolution (I', J'), for example based on a point spread function as calculated in step 2020 of FIG. 20, and a second iteration may provide a sub-pixel resolution (I, J), for example based on a point spread function as calculated in step 2070 of FIG. 20. The determination whether the point spread function is appropriately centered can be made based on a comparison between (I', J') and (I, J). For example, if the difference between I' and I and the difference between J' and J are both less than a pre-determined metric, then it can be concluded that the appropriately centered. An exemplary pre-determined metric may be within a range from about 0.1 microns to about 10 microns. For example, a value of 0.1 microns, 1 micron, or 10 microns may be used for the metric.

Where increased accuracy is desired, it may be desirable to use a larger frame size. For example, it may be possible to achieve a pixel resolution of 100×100 (or 100 micron resolution) by using a 101×101 frame size (covering a 10 mm×10 mm cornea area). Relatedly, it is possible to choose 10 microns as a sub-pixel resolution, or 0.1 pixels. Similarly, it may be possible to achieve a pixel resolution of 25×25 microns (or 25 micron resolution) by using a 401×401 frame size (still covering a 10 mm×10 mm cornea area). Relatedly, it is possible to choose 5 microns as a sub-pixel resolution, or 0.2 pixels. Optionally, it is also possible to choose 2.5 microns as a sub-pixel resolution, or 0.1 pixels, to be consistent with the previous case.

According to some embodiments, (i, j) can be considered as the first approximation of the center of the point spread function, and (I, J) can be considered a more accurate (sub-pixel accuracy) center of the point spread function. Because (I, J) are real numbers, the accuracy level provided by (I, J) is not limited to integers, and thus can provide a level of accuracy that is more precise than can be obtained by pixel resolution. Theoretically, the center of the frame is at (0, 0) but the center of the point spread function will typically not be at (0, 0) due to the fact of energy of the point spread function may not be symmetric. In some instances, the point spread function can be considered to have two centers, where one center is the maximum value pixel or pixel with the highest point spread function value, and another center is the center of mass. In practice, these two centers can be different. Often, it is the center of mass which is considered as the point spread function center. For example, if the point spread function has a dumbbell shape, the maximum value pixel may be in one of the two circles, but the center of mass is in-between the two circles.

Once the position values for centration (I, J) are obtained, the following formula can be used to determine the Zernike tip/tilt to apply in the pupil plane in order to move the point spread function toward the center.

$$Z2=Z2+I/(7*\text{scale})$$

$$Z3=Z3-J/(7*\text{scale})$$

Here, scale represents the scaling factor to apply the zero-padding. Z2 and Z3 represent wavefront Zernike numbers corresponding to the pupil plane.

Figures 22A, 22B:
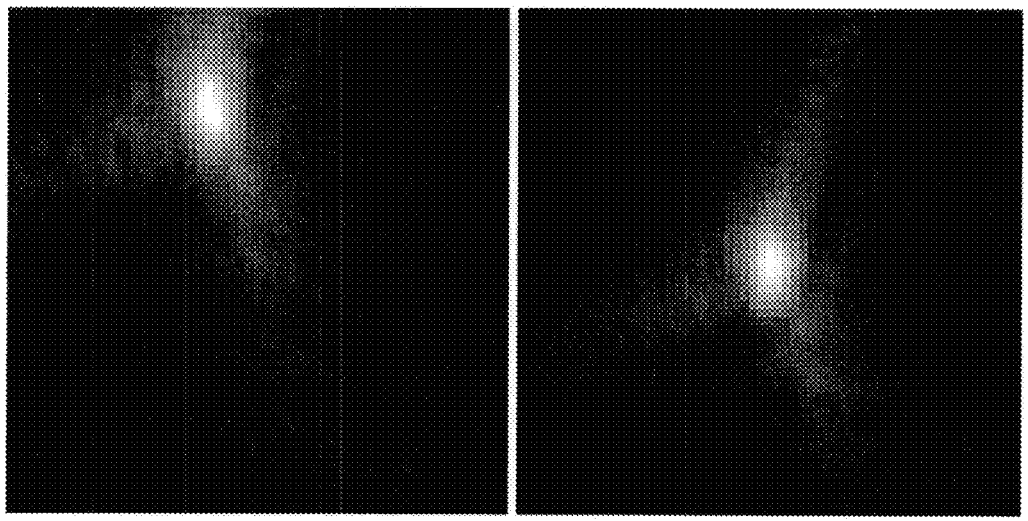
FIGS. 22A and 22B illustrate a decentered point spread function and a centered point spread function, respectively, according to embodiments of the present invention.

FIG. 22A shows an exemplary point spread function, which is de-centered with respect to the frame. Here, a portion of the point spread function energy is not within the field of view. FIG. 22B shows the resulting point spread function following the application of re-centration techniques as described herein. Here, the point spread function has been moved toward the center of the point spread function frame such that a greater portion of the point spread function is within the field. Accordingly, when performing a convolution, more point spread function energy is used when convolving with the FIG. 22B point spread function, as compared with the FIG. 22A point spread function. An algorithm for predicting the acuity or resolution, as discussed elsewhere herein, uses specific pixels, to determine contrast change and acuity measures. Hence, if a point spread function is not centered appropriately with respect to the frame, suboptimal results may be generated.

According to some embodiments, a convolution process can be performed as follows. Suppose h(x, y) stands for the point spread function of an optical system, such as a human eye. If s(x, y) represents a scene or an eye chart or even an eye chart letter, the optical image i(x, y) through the optical system can be described as a two-dimensional convolution as $$i(x, y) = h(x, y) \otimes s(x, y).$$

Typically, when the point spread function is calculated, it has a certain field of view, which can be affected by the aperture size of the optical system, the frame size, and the relative size of the wavefront data to the overall frame size. To get more detail of the point spread function, a zero-padding procedure can be performed to increase the resolution of the point spread function by making the frame size larger and adding padding zeros to the area outside of wavefront data. When zeros are padded, resolution increases and the field of view decreases. At some point, when the field of view is too small, part of the point spread function may be cut off, especially when the point spread function is significantly de-centered.

Figures 23A, 23B:
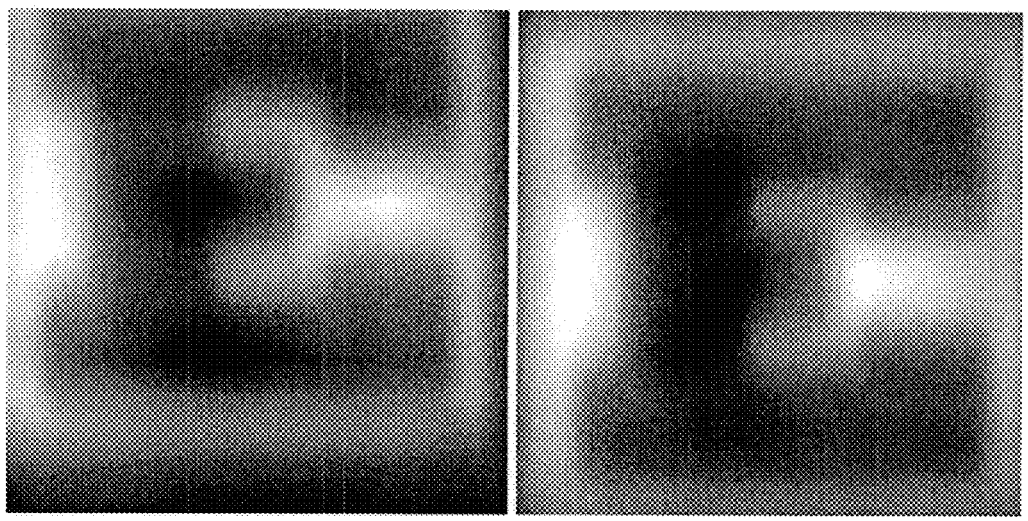
FIGS. 23A and 23B illustrate images corresponding to an eye chart letter E convolved with a decentered point spread function and a centered point spread function, respectively, according to embodiments of the present invention.

FIG. 23A shows an image corresponding to an eye chart letter E convolved with the point spread function of FIG. 22A, and FIG. 23B shows an image corresponding to an eye chart letter E convolved with the point spread function of FIG. 22B. As depicted here, the image of FIG. 23B is more centered than that of FIG. 23A. Hence, it is evident that in some cases centration of the point spread function can result in improved vision simulation and acuity evaluation. It has also been observed that when the point spread function is re-calculated with the re-centration, the CMTF values improve. Further, it has been observed that through-focus shows good results when used with a centered PSF. The extent of improvement may depend upon the field of view of the point spread function.

Figures 24A, 24B:
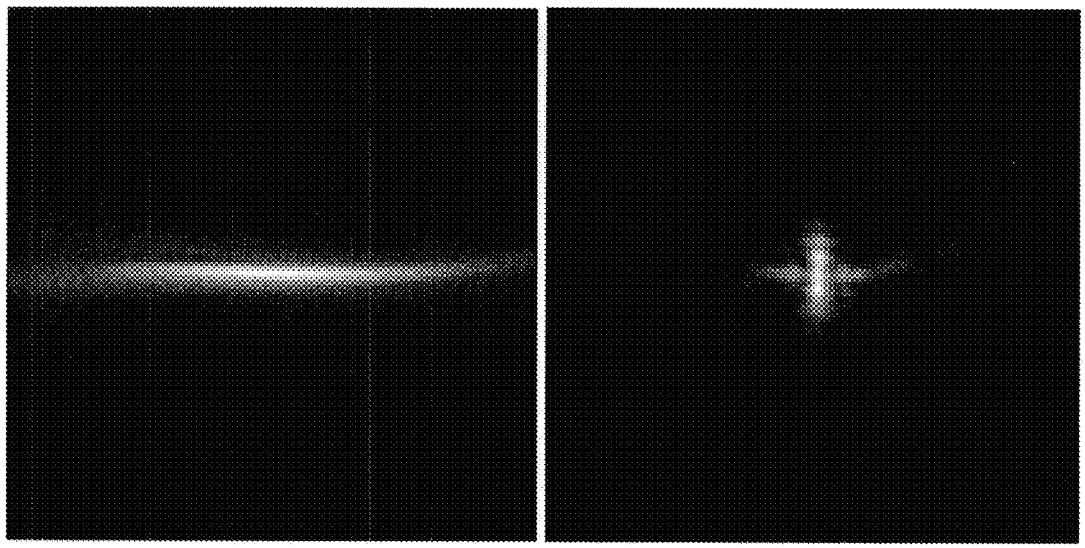
FIGS. 24A and 24B depict examples of centered point spread functions according to embodiments of the present invention.
Figures 25A, 25B:
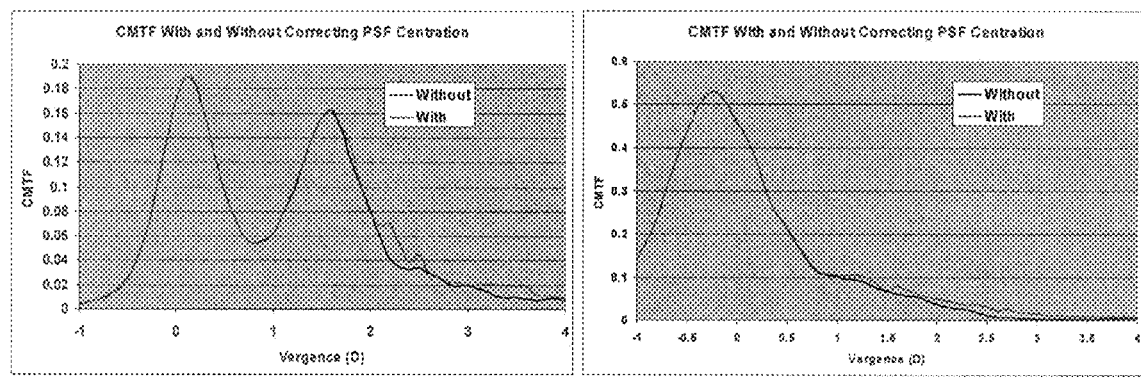
FIGS. 25A and 25B show examples of comparative compound modulation transfer function (CMTF) through-focus curves, according to embodiments of the present invention.

FIGS. 24A and 24B each show an example of a centered point spread function. Relatedly, FIGS. 25A and 25B each show comparative compound modulation transfer function (CMTF) through-focus curves, which illustrate the improvement in CMTF which is achieved by using a point spread function which has been centered according to the centration techniques described herein. As shown here, FIG. 24A corresponds with FIG. 25A, and FIG. 24B corresponds with FIG. 25B. The improvement is primarily evident in the right hand side of each chart, in the tail of the through-focus curves, because at a relatively large vergence, the defocus term makes the point spread function span a wide field of view. Without point spread function centration, a significant portion of the point spread function energy may be out of view. With a centration correction, however, the energy of the point spread function is in the field, making the CMTF curve improved. For FIGS. 25A and 25B, the CMTF parameters used include spatial frequencies at 10, 15, 20, and 30 cpd. For the point spread function, a 201×201 frame size and a polychromatic model were used, and a 6 mm pupil was assumed. The scale factor for zero-padding is 2.

Hence, embodiments of the present invention encompass techniques and algorithms for convolving eye chart letters, re-centration of point spread function, sub-pixel resolution of point spread function centration, and Zernike compensation for the point spread function decentration.

All patent filings, scientific journals, books, treatises, and other publications and materials discussed in this application are hereby incorporated by reference for all purposes. A variety of modifications are possible within the scope of the present invention. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with the current invention. The above systems are available from TRACEY Technologies of Bellaire, Tex., Wavelight of Erlangen, Germany, and Nidek, Inc. of Fremont, Calif., respectively. The invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to refractive laser corneal surgery.

Each of the calculations herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

The approaches of the present invention can be implemented on a variety of computer systems, including those with a 200 MHz CPU with 64 MB memory, and typically will be coded in a computer language such as C or C++. Simulations have successfully been run on a laptop computer with a 1.2 GHz CPU with 256 MB memory. The techniques of the present invention can also be implemented on faster and more robust computer systems.

The methods, systems, and devices of the present invention may be provided in one or more kits for such use. The kits may include a system for predicting an optical acuity measure of an eye. Such a system can include a module that determines a point spread function based on a wavefront measurement of an eye, a module that convolves a resolution target with the point spread function to produce an image, and a module that predicts the optical acuity measure of the eye based on the image. The kit can also include instructions to use the system to predict an optical acuity measure of an eye. Optionally, a kit may further include any of the other system components or devices described in relation to the present invention and any other materials or items relevant to the present invention. The instructions for use can set forth any of the methods as described above. Relatedly, the systems and devices of the present invention can be configured to carry out any of the method steps described herein.

While exemplary embodiments of the present invention have been described in detail for clarity of understanding, a variety of modifications and changes will be obvious to those of skill in the art. Hence, the scope of the claims is limited solely by the appended claims.

What is claimed is:

1. A method for determining an optical acuity measure of an eye, the method comprising:
    obtaining a first point spread function based on a wavefront measurement of an eye;
    determining whether the first point spread function is centered; and
        if the first point spread function is centered, convolving a target with the point spread function to produce an image, and determining the optical acuity measure of the eye based on the image; or
        if the first point spread function is not centered, modifying a Zernike tip term and a Zernike tilt term of the wavefront measurement, obtaining a second point spread function based on the wavefront measurement with modified Zernike terms, determining that the second point spread function is centered, convolving a target with the second point spread function to produce an image, and determining the optical acuity measure of the eye based on the image.

2. The method according to claim 1, wherein the step of determining whether the first point spread function is centered comprises calculating a diffraction limited point spread function, and correlating the diffraction limited point spread function with the first point spread function to provide a correlation matrix.

3. The method according to claim 2, further comprising searching the correlation matrix for a maximum value pixel.

4. The method according to claim 3, further comprising obtaining a sub-pixel resolution measure based on the maximum value pixel.

5. The method according to claim 1, wherein the step of determining whether the first point spread function is centered comprises determining whether a pre-determined metric is met.

6. The method according to claim 5, wherein the pre-determined metric comprises a value within a range from about 0.1 microns to about 10 microns.

7. The method according to claim 1, further comprising generating a vision treatment for the eye based on the optical acuity measure.

8. The method according to claim 7, further comprising administering the vision treatment to the eye.

9. A system for determining an optical acuity measure of an eye, the system comprising:
    a first module that obtains a first point spread function based on a wavefront measurement of an eye;
    a second module that determines whether the first point spread function is centered;
    a third module that convolves a target with the point spread function to produce an image and determines the optical acuity measure of the eye based on the image, if the first point spread function is centered; and
    a fourth module that modifies a Zernike tip term and a Zernike tilt term of the wavefront measurement, obtains a second point spread function based on the wavefront measurement with modified Zernike terms, determines that the second point spread function is centered, convolves a target with the second point spread function to produce an image, and determines the optical acuity measure of the eye based on the image, if the first point spread function is not centered.

10. The system according to claim 9, wherein the second module determines whether the first point spread function is centered at least in part by calculating a diffraction limited point spread function, and correlating the diffraction limited point spread function with the first point spread function to provide a correlation matrix.

11. The system according to claim 10, wherein the second module determines whether the first point spread function is centered at least in part by searching the correlation matrix for a maximum value pixel.

12. The system according to claim 11, wherein the second module determines whether the first point spread function is centered at least in part by obtaining a sub pixel resolution measure based on the maximum value pixel.

13. The system according to claim 9, wherein the second module determines whether the first point spread function is centered at least in part by determining whether a pre-determined metric is met.

14. The system according to claim 13, wherein the pre-determined metric comprises a value within a range from about 0.1 microns to about 10 microns.

15. A computer program product for determining an optical acuity measure of an eye, the computer program product comprising:

a first code for accepting a first point spread function based on a wavefront measurement of an eye;

a second code for determining whether the first point spread function is centered;

a third code for convolving a target with the point spread function to produce an image and determining the optical acuity measure of the eye based on the image, if the first point spread function is centered;

a fourth code for modifying a Zernike tip term and a Zernike tilt term of the wavefront measurement, obtaining a second point spread function based on the wavefront measurement with modified Zernike terms, determining that the second point spread function is centered, convolving a target with the second point spread function to produce an image, and determining the optical acuity measure of the eye based on the image, if the first point spread function is not centered; and a computer-readable medium that stores the codes.

16. The computer program product of claim 15, wherein the second code further comprises code for calculating a diffraction limited point spread function, and for correlating the diffraction limited point spread function with the first point spread function to provide a correlation matrix.

17. The computer program product of claim 16, wherein the second code further comprises code for searching the correlation matrix for a maximum value pixel.

18. The computer program product of claim 17, wherein the second code further comprises code for obtaining a sub pixel resolution measure based on the maximum value pixel.

19. The computer program product of claim 15, wherein the second code further comprises code for determining whether a pre-determined metric is met.

20. The computer program product of claim 19, wherein the pre-determined metric comprises a value within a range from about 0.1 microns to about 10 microns.

* * * * *